United States Patent
Sun et al.

(10) Patent No.: US 6,777,590 B2
(45) Date of Patent: Aug. 17, 2004

(54) CELL CYCLE NUCLEIC ACIDS, POLYPEPTIDES AND USES THEREOF

(75) Inventors: Yuejin Sun, Johnston, IA (US); Brian R. Dilkes, Tucson, AZ (US); Brian A. Larkins, Tucson, AZ (US); Keith S. Lowe, Johnston, IA (US); William J. Gordon-Kamm, Urbandale, IA (US); Ricardo A. Dante, Tucson, AZ (US)

(73) Assignees: Pioneer Hi-Bred International, Inc., Des Moines, IA (US); The Arizona Board of Regents on Behalf of the University of Arizona, Tucson, AZ (US)

( * ) Notice: Subject to any disclaimer, the term of this patent is extended or adjusted under 35 U.S.C. 154(b) by 476 days.

(21) Appl. No.: 09/470,526

(22) Filed: Dec. 22, 1999

(65) Prior Publication Data

US 2003/0041342 A1 Feb. 27, 2003

Related U.S. Application Data

(60) Provisional application No. 60/113,440, filed on Dec. 23, 1998.

(51) Int. Cl.[7] .................. C12N 15/29; C12N 15/82; A01H 5/00; A01H 5/10
(52) U.S. Cl. ............... 800/290; 536/23.6; 435/320.1; 435/419; 435/252.3; 435/254.11; 435/348; 800/298; 800/306; 800/312; 800/314; 800/320; 800/320.1; 800/320.2; 800/320.3; 800/322
(58) Field of Search ............. 536/23.6; 435/320.1, 435/419, 468, 252.3, 254.11, 348; 800/290, 298, 306, 312, 314, 320–320.3, 322

(56) References Cited

FOREIGN PATENT DOCUMENTS

| WO | WO 92/09685 | 6/1992 | ............ C12N/5/00 |
| WO | WO 99/49061 | 9/1999 | ............ C12N/15/62 |
| WO | WO 99/54489 | 10/1999 | ............ C12N/15/82 |
| WO | WO 99/66055 | 12/1999 | ............ C12N/15/82 |

OTHER PUBLICATIONS

Aligue et al, "Regulation of Schizosaccharomyces pombe Wee1 Tyrosine Kinase", May 1997, The Journal of Biological Chemistry, vol. 272, No. 20 pp. 13320–13325.*

Hemerly et al, "Dominant negative mutants of the cdc2 kinase uncouple cell division from iterative plant development", 1995, The Embo Journal, vol. 14, No. 16 pp. 3925–3936.*

Schutz et al, Genbank Accession AI065687, Jul. 24, 1998.*

Schutz et al., "ag91f10 maize inflorescence immature ear library Zea mays cDNA clone ag91f10 3', mRNA sequence", EMBL Accession No. AI065687, Jul. 27, 1998 (XP002140188).

Sun et al., "Characterization of maize (Zea mays L.) Wee1 and its activity in developing endosperm", *Proc. Natl. Acad. Sci. USA*, 96:4180–4185, 1999.

* cited by examiner

*Primary Examiner*—Elizabeth F. McElwain
*Assistant Examiner*—Cynthia Collins
(74) *Attorney, Agent, or Firm*—Pioneer Hi-Bred International, Inc.

(57) ABSTRACT

The invention provides isolated nucleic acids and their encoded proteins that are involved in cell cycle regulation. The invention further provides recombinant expression cassettes, host cells, transgenic plants, and antibody compositions. The present invention provides methods and compositions relating to altering cell cycle protein content, cell cycle progression and/or composition of plants.

17 Claims, 1 Drawing Sheet

SEQUENCE LISTING

<160> NUMBER OF SEQ ID NOS: 9

<210> SEQ ID NO 1
<211> LENGTH: 1582
<212> TYPE: DNA
<213> ORGANISM: Zea mays
<220> FEATURE:
<221> NAME/KEY: CDS
<222> LOCATION: (3)...(1211)

<400> SEQUENCE: 1

```
tc tgc acc ccg gac tac atc acg ccg gag atg ccg cag gtg gcc aac        47
   Cys Thr Pro Asp Tyr Ile Thr Pro Glu Met Pro Gln Val Ala Asn
    1               5                  10                 15 gag ttc gac gac gac gat aag gag aac atc ccc tgc cca aaa tct ccg       95
Glu Phe Asp Asp Asp Asp Lys Glu Asn Ile Pro Cys Pro Lys Ser Pro
                    20                  25                  30 gag aag tca gcg aac cct cgt agc aag cgg tac aga acc gat tgt tct      143
Glu Lys Ser Ala Asn Pro Arg Ser Lys Arg Tyr Arg Thr Asp Cys Ser
                35                  40                  45 ccc aaa gct cgg gag gtt acg gac ttc tct ttc gac cat cag att acg      191
Pro Lys Ala Arg Glu Val Thr Asp Phe Ser Phe Asp His Gln Ile Thr
            50                  55                  60 ccg gtt ctg ttt gac agc ttg act cga gat gat tcg gaa gaa gag cag      239
Pro Val Leu Phe Asp Ser Leu Thr Arg Asp Asp Ser Glu Glu Glu Gln
        65                  70                  75 ccg aag cag cct gcg ctg gaa aag agg ggt ggt tat gtc tcc cag tca      287
Pro Lys Gln Pro Ala Leu Glu Lys Arg Gly Gly Tyr Val Ser Gln Ser
 80                  85                  90                  95 gca gtg gct ctg cgt tgc cgg gtg atg cct ccg cca tgc gtc aag aat      335
Ala Val Ala Leu Arg Cys Arg Val Met Pro Pro Pro Cys Val Lys Asn
                    100                 105                 110 cca tac ctc aat acc gat cca tgc ata gat gct gct gtt tac ggt ggg      383
Pro Tyr Leu Asn Thr Asp Pro Cys Ile Asp Ala Ala Val Tyr Gly Gly
                115                 120                 125 agg cag tgc aac tca gca gta ttc tct cct tca att ggt ggt aat ggt      431
Arg Gln Cys Asn Ser Ala Val Phe Ser Pro Ser Ile Gly Gly Asn Gly
            130                 135                 140 ctt tca cgc tat cga act gat ttc cat gaa ata gag aaa att ggt tat      479
Leu Ser Arg Tyr Arg Thr Asp Phe His Glu Ile Glu Lys Ile Gly Tyr
        145                 150                 155 ggc aac ttc agt gtt gtg ttc aaa gtt ctg aat agg ata gac ggg tgc      527
Gly Asn Phe Ser Val Val Phe Lys Val Leu Asn Arg Ile Asp Gly Cys
160                 165                 170                 175 ttg tat gct gtt aaa cgg agc atc aag caa ttg cat aat gat atg gaa      575
Leu Tyr Ala Val Lys Arg Ser Ile Lys Gln Leu His Asn Asp Met Glu
                    180                 185                 190
```

| | | |
|---|---|---|
| agg agg caa gca gtg aaa gaa gtc caa gct atg gca gcc tta ggt tct<br>Arg Arg Gln Ala Val Lys Glu Val Gln Ala Met Ala Ala Leu Gly Ser<br>                195                      200                205 | 623 |
| cac gag aac ata gtt cga tat ttc acc tct tgg ttt gag aat gag caa<br>His Glu Asn Ile Val Arg Tyr Phe Thr Ser Trp Phe Glu Asn Glu Gln<br>    210                      215                      220 | 671 |
| ctt tat att cag atg gaa ctc tgc gac cgc tgt cta tct atg aat cgg<br>Leu Tyr Ile Gln Met Glu Leu Cys Asp Arg Cys Leu Ser Met Asn Arg<br>225                      230                      235 | 719 |
| aac cag cca gtg aag cgt ggg gaa gcc ctg gaa ctg ttg tat cag atc<br>Asn Gln Pro Val Lys Arg Gly Glu Ala Leu Glu Leu Leu Tyr Gln Ile<br>240                      245                    250                255 | 767 |
| tgc aaa ggc ttg gat ttc atg cac gaa cgt ggc ata gca cac ctt gat<br>Cys Lys Gly Leu Asp Phe Met His Glu Arg Gly Ile Ala His Leu Asp<br>                260                      265                      270 | 815 |
| gtg aag cct gat aat ata tat gtc aga aat ggt att tat aag ctc ggg<br>Val Lys Pro Asp Asn Ile Tyr Val Arg Asn Gly Ile Tyr Lys Leu Gly<br>                    275                      280                      285 | 863 |
| gat ttt ggc tgt gct aca ctt gtt aac cgg agt cta gca att gaa gat<br>Asp Phe Gly Cys Ala Thr Leu Val Asn Arg Ser Leu Ala Ile Glu Asp<br>        290                      295                      300 | 911 |
| gga gat tca cgc tat atg cct ccg gaa atg ctg aat gat aag tat gag<br>Gly Asp Ser Arg Tyr Met Pro Pro Glu Met Leu Asn Asp Lys Tyr Glu<br>305                      310                      315 | 959 |
| cat ctc gac aag gtt gat atc ttt tct ctt ggg gca gcc gtc tat gag<br>His Leu Asp Lys Val Asp Ile Phe Ser Leu Gly Ala Ala Val Tyr Glu<br>320                      325                    330                335 | 1007 |
| cta ata aga ggc acc ccg ctt ccc gag tct gga tct cac ttt aca agc<br>Leu Ile Arg Gly Thr Pro Leu Pro Glu Ser Gly Ser His Phe Thr Ser<br>                340                      345                      350 | 1055 |
| att aga gag ggt aag atc gca ttg ctt cca ggg tgc ccg atg cag ttt<br>Ile Arg Glu Gly Lys Ile Ala Leu Leu Pro Gly Cys Pro Met Gln Phe<br>                    355                      360                      365 | 1103 |
| caa agc tta atc aag tct atg atg gac cct gat ccg gtg agg cgg cct<br>Gln Ser Leu Ile Lys Ser Met Met Asp Pro Asp Pro Val Arg Arg Pro<br>        370                      375                      380 | 1151 |
| tca gca aag gag atc ctg aga cac cct tcc ttt gac aag ctc cac aag<br>Ser Ala Lys Glu Ile Leu Arg His Pro Ser Phe Asp Lys Leu His Lys<br>385                      390                    395 | 1199 |
| gcc tca tcg aag tagaagtgct gccgcgcccc catcagatca gagcagccgg<br>Ala Ser Ser Lys<br>400 | 1251 |
| caaagggaat tccgcagctg cgtcacattc accgtcagct gctcccaatt tttggtgtat | 1311 |
| ctatctatct ctatgcgtgt gccatgtgcc ctgttctgat actgtagaag atggctggaa | 1371 |
| acgaagcagg gatctgattt taattccagg aactggagca cgagcagcgt ctgtaaagga | 1431 |
| ctaaaggctg tggctgctgt tgtgttaagg ttgtgcctct cttttggttt ctgatgcacg | 1491 |
| cttggaacca tcaaccctgt gccttttttt ggggtgcttg ttatcagttg catttgggca | 1551 |
| gcgaatgcta atttggatcc aaaaaaaaaa a | 1582 |

<210> SEQ ID NO 2
<211> LENGTH: 403
<212> TYPE: PRT
<213> ORGANISM: Zea mays

<400> SEQUENCE: 2

Cys Thr Pro Asp Tyr Ile Thr Pro Glu Met Pro Gln Val Ala Asn Glu
1               5                    10                   15

```
                                    -continued

Phe Asp Asp Asp Lys Glu Asn Ile Pro Cys Pro Lys Ser Pro Glu
            20                  25              30

Lys Ser Ala Asn Pro Arg Ser Lys Arg Tyr Arg Thr Asp Cys Ser Pro
        35                  40                  45

Lys Ala Arg Glu Val Thr Asp Phe Ser Phe Asp His Gln Ile Thr Pro
    50                  55                  60

Val Leu Phe Asp Ser Leu Thr Arg Asp Asp Ser Glu Glu Glu Gln Pro
65                  70                  75                  80

Lys Gln Pro Ala Leu Glu Lys Arg Gly Gly Tyr Val Ser Gln Ser Ala
                85                  90                  95

Val Ala Leu Arg Cys Arg Val Met Pro Pro Cys Val Lys Asn Pro
            100                 105                 110

Tyr Leu Asn Thr Asp Pro Cys Ile Asp Ala Ala Val Tyr Gly Gly Arg
            115                 120                 125

Gln Cys Asn Ser Ala Val Phe Ser Pro Ser Ile Gly Gly Asn Gly Leu
    130                 135                 140

Ser Arg Tyr Arg Thr Asp Phe His Glu Ile Glu Lys Ile Gly Tyr Gly
145                 150                 155                 160

Asn Phe Ser Val Val Phe Lys Val Leu Asn Arg Ile Asp Gly Cys Leu
                165                 170                 175

Tyr Ala Val Lys Arg Ser Ile Lys Gln Leu His Asn Asp Met Glu Arg
            180                 185                 190

Arg Gln Ala Val Lys Glu Val Gln Ala Met Ala Ala Leu Gly Ser His
            195                 200                 205

Glu Asn Ile Val Arg Tyr Phe Thr Ser Trp Phe Glu Asn Glu Gln Leu
    210                 215                 220

Tyr Ile Gln Met Glu Leu Cys Asp Arg Cys Leu Ser Met Asn Arg Asn
225                 230                 235                 240

Gln Pro Val Lys Arg Gly Glu Ala Leu Glu Leu Leu Tyr Gln Ile Cys
                245                 250                 255

Lys Gly Leu Asp Phe Met His Glu Arg Gly Ile Ala His Leu Asp Val
            260                 265                 270

Lys Pro Asp Asn Ile Tyr Val Arg Asn Gly Ile Tyr Lys Leu Gly Asp
            275                 280                 285

Phe Gly Cys Ala Thr Leu Val Asn Arg Ser Leu Ala Ile Glu Asp Gly
            290                 295                 300

Asp Ser Arg Tyr Met Pro Pro Glu Met Leu Asn Asp Lys Tyr Glu His
305                 310                 315                 320

Leu Asp Lys Val Asp Ile Phe Ser Leu Gly Ala Ala Val Tyr Glu Leu
            325                 330                 335

Ile Arg Gly Thr Pro Leu Pro Glu Ser Gly Ser His Phe Thr Ser Ile
            340                 345                 350

Arg Glu Gly Lys Ile Ala Leu Leu Pro Gly Cys Pro Met Gln Phe Gln
            355                 360                 365

Ser Leu Ile Lys Ser Met Met Asp Pro Asp Pro Val Arg Arg Pro Ser
    370                 375                 380

Ala Lys Glu Ile Leu Arg His Pro Ser Phe Asp Lys Leu His Lys Ala
385                 390                 395                 400

Ser Ser Lys

<210> SEQ ID NO 3
<211> LENGTH: 20
<212> TYPE: DNA
<213> ORGANISM: Zea mays
```

```
<220> FEATURE:
<221> NAME/KEY: CDS
<222> LOCATION: (1)...(20)

<400> SEQUENCE: 3 tgc acc ccg gac tac atc ac                                          20
Cys Thr Pro Asp Tyr Ile
  1               5

<210> SEQ ID NO 4
<211> LENGTH: 20
<212> TYPE: DNA
<213> ORGANISM: Zea mays
<220> FEATURE:
<221> NAME/KEY: CDS
<222> LOCATION: (1)...(20)

<400> SEQUENCE: 4 ggc gcg gca gca ctt cta ct                                          20
Gly Ala Ala Ala Leu Leu
  1               5

<210> SEQ ID NO 5
<211> LENGTH: 20
<212> TYPE: DNA
<213> ORGANISM: Zea mays
<220> FEATURE:
<221> NAME/KEY: CDS
<222> LOCATION: (1)...(20)

<400> SEQUENCE: 5 tct gca ccc cgg act aca tc                                          20
Ser Ala Pro Arg Thr Thr
  1               5

<210> SEQ ID NO 6
<211> LENGTH: 20
<212> TYPE: DNA
<213> ORGANISM: Zea mays
<220> FEATURE:
<221> NAME/KEY: CDS
<222> LOCATION: (1)...(20)

<400> SEQUENCE: 6 ggc aca tgg cac acg cat ag                                          20
Gly Thr Trp His Thr His
  1               5

<210> SEQ ID NO 7
<211> LENGTH: 20
<212> TYPE: DNA
<213> ORGANISM: Zea mays
<220> FEATURE:
<221> NAME/KEY: CDS
<222> LOCATION: (1)...(20)

<400> SEQUENCE: 7 ggc gcg gca gca ctt cta ct                                          20
Gly Ala Ala Ala Leu Leu
  1               5

<210> SEQ ID NO 8
<211> LENGTH: 1959
<212> TYPE: DNA
<213> ORGANISM: zea mays
<220> FEATURE:
<221> NAME/KEY: CDS
<222> LOCATION: (1)...(1576)
```

<400> SEQUENCE: 8

```
ggc acg agg ccg cgc ggc ggc aag gcg cgc cgc gcc gcg ccc ggg gcc      48
Gly Thr Arg Pro Arg Gly Gly Lys Ala Arg Arg Ala Ala Pro Gly Ala
  1               5                  10                  15 gcc tcg gcg gtc aag ccc gcc aag gcc gac ggg agg tcg ccg tcg gga      96
Ala Ser Ala Val Lys Pro Ala Lys Ala Asp Gly Arg Ser Pro Ser Gly
             20                  25                  30 gag ctc tcg ctg cag ctg gag cac gtc tcc ctc acc tcc ttg ctc tcc     144
Glu Leu Ser Leu Gln Leu Glu His Val Ser Leu Thr Ser Leu Leu Ser
         35                  40                  45 gac cgc cgc ccc gca tcc ggg ctc acg cgc ttc gag gtg ctc cta gag     192
Asp Arg Arg Pro Ala Ser Gly Leu Thr Arg Phe Glu Val Leu Leu Glu
     50                  55                  60 gaa gag gag tcg ggc tgc tac cgc gcc gac ccg acc ccg cag ccg ccg     240
Glu Glu Glu Ser Gly Cys Tyr Arg Ala Asp Pro Thr Pro Gln Pro Pro
 65                  70                  75                  80 cga ctt cct gag cca caa tct atg ccc ccg ccg ccg ccg ccg ccg         288
Arg Leu Pro Glu Pro Gln Ser Met Pro Pro Pro Pro Pro Pro Pro
                 85                  90                  95 atc tcg cag gca tcg ccg gtg gac gca gac gag acc atg gag gag aag     336
Ile Ser Gln Ala Ser Pro Val Asp Ala Asp Glu Thr Met Glu Glu Lys
            100                 105                 110 gat tgc tgc atc ctc agc cag gat ttc ttc tgc acc ccg gac tac atc     384
Asp Cys Cys Ile Leu Ser Gln Asp Phe Phe Cys Thr Pro Asp Tyr Ile
        115                 120                 125 acg ccg gag atg ccg cag gtg gcc aac gag ttc gac gac gac gac aag     432
Thr Pro Glu Met Pro Gln Val Ala Asn Glu Phe Asp Asp Asp Asp Lys
    130                 135                 140 gag aac atc ccc tgc cca aaa tct ccg gag aag tca gcg aac cct cgt     480
Glu Asn Ile Pro Cys Pro Lys Ser Pro Glu Lys Ser Ala Asn Pro Arg
145                 150                 155                 160 agc aag cgg tac aga acc gat tgt tct ccc aaa gct cgg gag gtt acg     528
Ser Lys Arg Tyr Arg Thr Asp Cys Ser Pro Lys Ala Arg Glu Val Thr
                165                 170                 175 gac ttc tct ttc gac cat cag att acg ccg gtt ctg ttt gac agc ctg     576
Asp Phe Ser Phe Asp His Gln Ile Thr Pro Val Leu Phe Asp Ser Leu
            180                 185                 190 act cga gat gat tcg gaa gaa gag cag ccg aag cag cct gcg ctg gaa     624
Thr Arg Asp Asp Ser Glu Glu Glu Gln Pro Lys Gln Pro Ala Leu Glu
        195                 200                 205 aag agg ggt ggt tat gtc tcc cag tca gca gtg gct ctg cgt tgc cgg     672
Lys Arg Gly Gly Tyr Val Ser Gln Ser Ala Val Ala Leu Arg Cys Arg
    210                 215                 220 gtg atg cct ccg cca tgc gtc aag aat cca tac ctc aat acc gat cca     720
Val Met Pro Pro Pro Cys Val Lys Asn Pro Tyr Leu Asn Thr Asp Pro
225                 230                 235                 240 tgc ata gat gct gct gtt tac ggt ggg agg cag tgc aac tca gca gta     768
Cys Ile Asp Ala Ala Val Tyr Gly Gly Arg Gln Cys Asn Ser Ala Val
                245                 250                 255 ttt tct cct tca att ggt ggt aat ggt ctt tca cgc tat cga act gat     816
Phe Ser Pro Ser Ile Gly Gly Asn Gly Leu Ser Arg Tyr Arg Thr Asp
            260                 265                 270 ttc cat gaa ata gag aaa att ggt tat ggc aac ttc agt gtt gtg ttc     864
Phe His Glu Ile Glu Lys Ile Gly Tyr Gly Asn Phe Ser Val Val Phe
        275                 280                 285 aaa gtt ctg aat agg ata gac ggg tgc ttg tat gct gtt aaa cgg agc     912
Lys Val Leu Asn Arg Ile Asp Gly Cys Leu Tyr Ala Val Lys Arg Ser
    290                 295                 300 atc aag caa ttg cat aat gat atg gaa agg agg caa gca gtg aaa gaa     960
```

```
Ile Lys Gln Leu His Asn Asp Met Glu Arg Arg Gln Ala Val Lys Glu
305                 310                 315                 320 gtc caa gct atg gca gcc tta ggt tct cac gag aac ata gtt cga tat      1008
Val Gln Ala Met Ala Ala Leu Gly Ser His Glu Asn Ile Val Arg Tyr
                325                 330                 335 ttc acc tct tgg ttt gag aat gag caa ctt tat att cag atg gaa ctc      1056
Phe Thr Ser Trp Phe Glu Asn Glu Gln Leu Tyr Ile Gln Met Glu Leu
        340                 345                 350 tgc gac cgc tgt cta tct atg aat cgg aac cag cca gtg aag cgt ggg      1104
Cys Asp Arg Cys Leu Ser Met Asn Arg Asn Gln Pro Val Lys Arg Gly
    355                 360                 365 gaa gcc ctg gaa ctg ttg tat cag atc tgc aaa ggc ttg gat ttc atg      1152
Glu Ala Leu Glu Leu Leu Tyr Gln Ile Cys Lys Gly Leu Asp Phe Met
370                 375                 380 cac gaa cgt ggc ata gca cac ctt gat gtg aag cct gat aac ata tat      1200
His Glu Arg Gly Ile Ala His Leu Asp Val Lys Pro Asp Asn Ile Tyr
385                 390                 395                 400 gtc aga aat ggt att tat aag ctc ggg gat ttt ggc tgt gct aca ctt      1248
Val Arg Asn Gly Ile Tyr Lys Leu Gly Asp Phe Gly Cys Ala Thr Leu
                405                 410                 415 gtt aac cgg agt cta gca att gaa gat gga gat tca cgc tat atg cct      1296
Val Asn Arg Ser Leu Ala Ile Glu Asp Gly Asp Ser Arg Tyr Met Pro
        420                 425                 430 ccg gaa atg ctg aat gat aag tat gag cat ctt gac aag gtt gat atc      1344
Pro Glu Met Leu Asn Asp Lys Tyr Glu His Leu Asp Lys Val Asp Ile
    435                 440                 445 ttt tct ctt ggg gca gcc gtc tat gag cta ata aga ggc acc ccg ctt      1392
Phe Ser Leu Gly Ala Ala Val Tyr Glu Leu Ile Arg Gly Thr Pro Leu
450                 455                 460 cct gag tct gga tct cac ttt aca agc att aga gag ggt aag atc gca      1440
Pro Glu Ser Gly Ser His Phe Thr Ser Ile Arg Glu Gly Lys Ile Ala
465                 470                 475                 480 ttg ctt cca ggg tgc ccg atg cag ttt caa agt tta atc aag tct atg      1488
Leu Leu Pro Gly Cys Pro Met Gln Phe Gln Ser Leu Ile Lys Ser Met
                485                 490                 495 atg gac cct gat ccg gtg agg cgg cct tca gca aag gag atc ctg aga      1536
Met Asp Pro Asp Pro Val Arg Arg Pro Ser Ala Lys Glu Ile Leu Arg
        500                 505                 510 cac cct tcg ttt gac aag ctc cac aag gcc tca tcg aag t agaagtgctg    1586
His Pro Ser Phe Asp Lys Leu His Lys Ala Ser Ser Lys
    515                 520                 525 ccgcgccccc gtcagatcag agcagccggc aaagggaatt ccgcagctgc gtcacattca   1646
ccatcagctg ctcccaattt tgtgtatct atctatctat atgcgtgtgc catgtgccct    1706
gttctgatac tgtagaagat ggttggaaac gaagcaggga tctgatttta actccaggaa   1766
ctggagcacg agcagcgtct gtaaaggact aaaaggctgt tgctgctgtt gtgttaaggt   1826
tgtgcctctt tttggtttct gatgcacgct tgaaaccatc aaccctgtgc cttttttgg    1886 ggtgcttgtt atcagttgca tctggacagc gaatgctaat ttggaatttt tctctccagt   1946
tagcccttaa aaa                                                     1959

<210> SEQ ID NO 9
<211> LENGTH: 525
<212> TYPE: PRT
<213> ORGANISM: zea mays

<400> SEQUENCE: 9

Gly Thr Arg Pro Arg Gly Gly Lys Ala Arg Arg Ala Ala Pro Gly Ala
1               5                   10                  15
```

```
Ala Ser Ala Val Lys Pro Ala Lys Ala Asp Gly Arg Ser Pro Ser Gly
            20                  25                  30

Glu Leu Ser Leu Gln Leu Glu His Val Ser Leu Thr Ser Leu Leu Ser
            35                  40                  45

Asp Arg Arg Pro Ala Ser Gly Leu Thr Arg Phe Glu Val Leu Leu Glu
        50                  55                  60

Glu Glu Glu Ser Gly Cys Tyr Arg Ala Asp Pro Thr Pro Gln Pro Pro
65                  70                  75                  80

Arg Leu Pro Glu Pro Gln Ser Met Pro Pro Pro Pro Pro Pro Pro Pro
                85                  90                  95

Ile Ser Gln Ala Ser Pro Val Asp Ala Asp Glu Thr Met Glu Glu Lys
            100                 105                 110

Asp Cys Cys Ile Leu Ser Gln Asp Phe Phe Cys Thr Pro Asp Tyr Ile
            115                 120                 125

Thr Pro Glu Met Pro Gln Val Ala Asn Glu Phe Asp Asp Asp Asp Lys
        130                 135                 140

Glu Asn Ile Pro Cys Pro Lys Ser Pro Glu Lys Ser Ala Asn Pro Arg
145                 150                 155                 160

Ser Lys Arg Tyr Arg Thr Asp Cys Ser Pro Lys Ala Arg Glu Val Thr
                165                 170                 175

Asp Phe Ser Phe Asp His Gln Ile Thr Pro Val Leu Phe Asp Ser Leu
            180                 185                 190

Thr Arg Asp Asp Ser Glu Glu Glu Gln Pro Lys Gln Pro Ala Leu Glu
        195                 200                 205

Lys Arg Gly Gly Tyr Val Ser Gln Ser Ala Val Ala Leu Arg Cys Arg
210                 215                 220

Val Met Pro Pro Pro Cys Val Lys Asn Pro Tyr Leu Asn Thr Asp Pro
225                 230                 235                 240

Cys Ile Asp Ala Ala Val Tyr Gly Gly Arg Gln Cys Asn Ser Ala Val
                245                 250                 255

Phe Ser Pro Ser Ile Gly Gly Asn Gly Leu Ser Arg Tyr Arg Thr Asp
            260                 265                 270

Phe His Glu Ile Glu Lys Ile Gly Tyr Gly Asn Phe Ser Val Val Phe
        275                 280                 285

Lys Val Leu Asn Arg Ile Asp Gly Cys Leu Tyr Ala Val Lys Arg Ser
        290                 295                 300

Ile Lys Gln Leu His Asn Asp Met Glu Arg Arg Gln Ala Val Lys Glu
305                 310                 315                 320

Val Gln Ala Met Ala Ala Leu Gly Ser His Glu Asn Ile Val Arg Tyr
                325                 330                 335

Phe Thr Ser Trp Phe Glu Asn Glu Gln Leu Tyr Ile Gln Met Glu Leu
            340                 345                 350

Cys Asp Arg Cys Leu Ser Met Asn Arg Asn Gln Pro Val Lys Arg Gly
        355                 360                 365

Glu Ala Leu Glu Leu Leu Tyr Gln Ile Cys Lys Gly Leu Asp Phe Met
    370                 375                 380

His Glu Arg Gly Ile Ala His Leu Asp Val Lys Pro Asp Asn Ile Tyr
385                 390                 395                 400

Val Arg Asn Gly Ile Tyr Lys Leu Gly Asp Phe Gly Cys Ala Thr Leu
                405                 410                 415

Val Asn Arg Ser Leu Ala Ile Glu Asp Gly Asp Ser Arg Tyr Met Pro
        420                 425                 430
```

```
                Pro Glu Met Leu Asn Asp Lys Tyr Glu His Leu Asp Lys Val Asp Ile
                        435                 440                 445

Phe Ser Leu Gly Ala Ala Val Tyr Glu Leu Ile Arg Gly Thr Pro Leu
                        450                 455                 460

Pro Glu Ser Gly Ser His Phe Thr Ser Ile Arg Glu Gly Lys Ile Ala
                465                 470                 475                 480

Leu Leu Pro Gly Cys Pro Met Gln Phe Gln Ser Leu Ile Lys Ser Met
                                485                 490                 495

Met Asp Pro Asp Pro Val Arg Arg Pro Ser Ala Lys Glu Ile Leu Arg
                                500                 505                 510

His Pro Ser Phe Asp Lys Leu His Lys Ala Ser Ser Lys
                        515                 520                 525
```

CELL CYCLE NUCLEIC ACIDS, POLYPEPTIDES AND USES THEREOF

This application claims priority under 35 USC 119 to U.S. Ser. No. 60/113,440 filed Dec. 23, 1998, the disclosure of which is incorporated herein by reference.

TECHNICAL FIELD

The present invention relates generally to plant molecular biology. More specifically, it relates to nucleic acids and methods for modulating their expression in plants.

BACKGROUND OF THE INVENTION

Cell division plays a crucial role during all phases of plant development. The continuation of organogenesis and growth responses to a changing environment requires precise spatial, temporal and developmental regulation of cell division activity in meristems (and in cells with the capability to form new meristems such as in lateral root formation). Such control of cell division is also important in organs themselves (i.e. separate from meristems per se), for example, in leaf expansion, secondary growth, and endoreduplication.

A complex network controls cell proliferation in eukaryotes. Various regulatory pathways communicate environmental constraints, such as nutrient availability, mitogenic signals such as growth factors or hormones, or developmental cues such as the transition from vegetative to reproductive. Ultimately, these regulatory pathways control the timing, frequency (rate), plane and position of cell divisions.

Plants have unique developmental features that distinguish them from other eukaryotes. Plant cells do not migrate, and thus only cell division, expansion and programmed cell death affect morphogenesis. Organs are formed throughout the entire life span of the plant from specialized regions called meristems. In addition, many differentiated cells have the potential to both dedifferentiate and to reenter the cell cycle. There are also numerous examples of plant cell types that undergo endoreduplication, a process involving nuclear multiplication without cytokinesis. The study of plant cell cycle control genes is expected to contribute to the understanding of these unique phenomena. (O. Shaul et al., *Regulation of Cell Division in Arabidopsis, Critical Reviews in Plant Sciences*, 15(2):97–112 (1996)).

Current transformation technology provides an opportunity to engineer plants with desired traits. Major advances in plant transformation have occurred over the last few years. However, in many major crop plants, serious genotype limitations still exist. Transformation of some agronomically important crop plants continues to be both difficult and time consuming. For example, it is difficult to obtain a culture response from some maize varieties. Typically, a suitable culture response has been obtained by optimizing medium components and/or explant material and source. This has led to success in some genotypes. While, transformation of model genotypes is efficient, the process of introgressing transgenes into production inbreds is laborious, expensive and time consuming. It would save considerable time and money if genes could be introduced into and evaluated directly in commercial hybrids.

There is evidence to suggest that cells must be dividing for transformation to occur. It has also been observed that dividing cells represent only a fraction of cells that transiently express a transgene. Furthermore, the presence of damaged DNA in non-plant systems (similar to DNA introduced by particle gun or other physical means) has been well documented to rapidly induce cell cycle arrest (W. Siede, *Cell cycle arrest in response to DNA damage: lessons from yeast*, Mutation Res. 337(2:73–84).

Current methods for genetic engineering in maize require a specific cell type as the recipient of new DNA. These cells are found in relatively undifferentiated, rapidly growing callus cells or on the scutellar surface of the immature embryo (which gives rise to callus). Irrespective of the delivery method currently used, DNA is introduced into literally thousands of cells, yet transformants are recovered at frequencies of $10^{-5}$ relative to transiently-expressing cells. Exacerbating this problem, the trauma that accompanies DNA introduction directs recipient cells into cell cycle arrest and accumulating evidence suggests that many of these cells are directed into apoptosis or programmed cell death. (Reference Bowen et al., International Plant Mol. Biol. Meetings, Tucson, Ariz. 1991). Therefore it would be desirable to provide improved methods capable of increasing transformation efficiency in a number of cell types.

In spite of increases in yield and harvested area worldwide, it is predicted that over the next ten years, meeting the demand for corn will require an additional 20% increase over current production (Dowswell, C. R., Paliwal, R. L., Cantrell, R. P., 1996, Maize in the Third World, Westview Press, Boulder, Colo.).

The components most often associated with maize productivity are grain yield or whole-plant harvest for animal feed (in the forms of silage, fodder, or stover). Thus the relative growth of the vegetative or reproductive organs might be preferred, depending on the ultimate use of the crop. Whether the whole plant or the ear are harvested, overall yield will depend strongly on vigor and growth rate. It would therefore be valuable to develop new methods that contribute to the increase in crop yield.

The proteins encoded by the wee1 polynucleotides range from approximately 107 kD in *Saccharomyces cerevisiae* to 68 kD in Xenopus. The WEE1 kinase (or functional homologues such as Mik1) preferentially phosphorylate tyrosine 15 (or 14) on the central cell cycle regulatory protein p34$^{cdc2}$. Such phosphorylation prevents p34$^{cdc2}$/cyclin-B complex binding with ATP, effectively blocking the transition from G2 into mitosis. Most of the variations in amino acid sequences of WEE1 are in the amino-terminus, while the carboxy end of these genes are relatively conserved. (Mueller et al. 1995). The carboxyl terminus and the central portion of the WEE1 protein from *S. pombe* contain the protein kinase domains and sequences crucial for substrate recognition and catalysis (Aligue et al., 1997). The wee1 gene was first isolated in yeast,(Russel and Nurse, 1987) and later in multicellular eukaryotic systems such as humans (Igarashi et al., 1993), Drosophila (Campbell et al., 1995), Xenopus (Mueller et a., 1954) and mouse (Honda et al., 1995). No wee1 homologs have been reported in plants to date.

SUMMARY OF THE INVENTION

The invention provides isolated nucleic acids and their encoded proteins that are involved in cell cycle regulation. The invention further provides recombinant expression cassettes, host cells, transgenic plants, and antibody compositions. The present invention provides methods and compositions relating to altering cell cycle protein content, cell cycle progression and/or composition of plants.

Definitions

The term "isolated" refers to material, such as a nucleic acid or a protein, which is: (1) substantially or essentially free from components which normally accompany or interact with the material as found in its naturally occurring environment or (2) if the material is in its natural environment, the material has been altered by deliberate human intervention to a composition and/or placed at a locus in the cell other than the locus native to the material.

As used herein, "plant" includes but is not limited to plant cells, plant tissue and plant seeds.

As used herein, "nucleic acid" means a polynucleotide and includes single or double-stranded polymer of deoxyribonucleotide or ribonucleotide bases. Nucleic acids may also include modified nucleotides that permit correct read through by a polymerase and do not alter the expression of a polypeptide encoded by the polynucleotide.

As used herein, "polypeptide" means proteins, protein fragments, modified proteins, amino acid sequences and synthetic amino acid sequences. The polypeptide can be glycosylated or not.

As used herein, "promoter" includes reference to a region of DNA upstream from the start of transcription and involved in recognition and binding of RNA polymerase and other proteins to initiate transcription.

By "fragment" is intended a portion of the nucleotide sequence or a portion of the amino acid sequence and hence protein encoded thereby. Preferably fragments of a nucleotide sequence may encode protein fragments that retain the biological activity of the native nucleic acid. However, fragments of a nucleotide sequence which are useful as hybridization probes generally do not encode fragment proteins retaining biological activity. Fragments of a nucleotide sequence are generally greater than 10 nucleotides, preferably at least 20 nucleotides and up to the entire nucleotide sequence encoding the proteins of the invention. Generally probes are less than 1000 nucleotides and preferably less than 500 nucleotides. Fragments of the invention include antisense sequences used to decrease expression of the inventive nucleic acids. Such antisense fragments may vary in length ranging from at least about 20 nucleotides, about 50 nucleotides, about 100 nucleotides, up to and including the entire coding sequence.

By "variants" is intended substantially similar sequences. Generally, nucleic acid sequence variants of the invention will have at least 50%, 60, 70%, or preferably 80%, more preferably at least 90% and most preferably at least 95% sequence identity to the native nucleotide sequence.

Generally, polypeptide sequence variants of the invention will have at least about 55%, 60%, 70%, 80%, or preferably at least about 90% and more preferably at least about 95% sequence identity to the native protein.

As used herein, "sequence identity" or "identity" in the context of two nucleic acid or polypeptide sequences includes reference to the residues in the two sequences that are the same when aligned for maximum correspondence over a specified comparison window. An indication that two peptide sequences are substantially identical is that one peptide is immunologically reactive with antibodies raised against the second peptide. A polypeptide is substantially identical to a second polypeptide, for example, where the two polypeptides differ only by a conservative substitution.

For purposes of defining the present invention, the Gap 10 program in the Wisconsin Genetics Software Package using default parameters is used, Genetics Computer Group (GCG), 575 Science Dr., Madison, Wis., USA. The algorithm used for the GAP program is that of Needleman and Wunsch (*J. Mol. Biol.* 48:443–453 [1970]). The parameters used are as follows: for nucleotide comparisons the gap creation penalty=50, gap extension penalty=3; for amino acid comparisons the gap creation penalty=12, the gap extension penalty=4.

By "functionally equivalent" is intended that the sequence of the variant defines a chain that produces a protein having substantially the same biological effect as the native protein of interest.

DETAILED DESCRIPTION OF THE INVENTION

Figure 1:
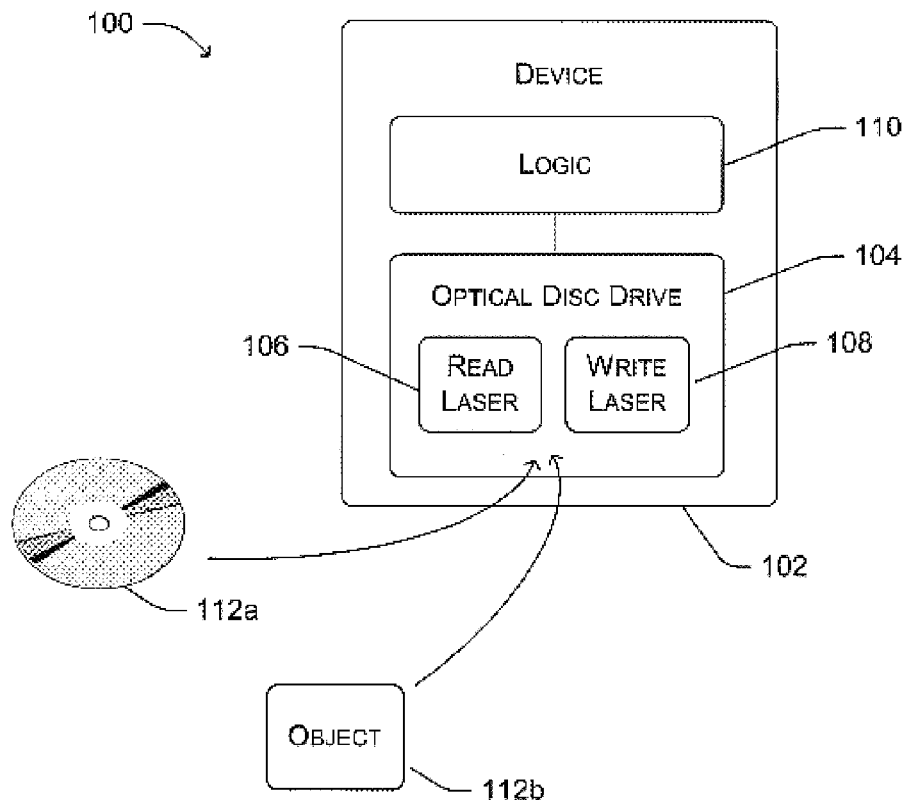
FIG. 1 demonstrates an overexpression of ZmWee1 in *S. pombe* causing cell enlargement. *S. pombe* cells were transformed with pREP1 (A) or pREP1 expressing ZmWee1 (B). Morphology of the cells was analyzed by light microscopy; both samples are shown at the same magnification.

A wee1 homologue from maize, zmwee1, whose activity resembles related protein tyrosine kinases from other eukaryotes has been isolated and characterized. ZMWEE1 is encoded by a single gene, and its RNA is relatively abundant in maize leaf, root, shoot, and other tissues. In addition, zmwee1 transcripts accumulated in endosperm tissue between 9 and 17 DAP. During this period of development, endosperm nuclei commence multiple cycles of endoreduplication, which involves S-phase with no intervening M-phase (Kowles and Philips, 1985).

Nucleic Acids

The present invention relates to an isolated nucleic acid comprising a member selected from the group consisting of:
(a) a polynucleotide that encodes a polypeptide of SEQ ID NO: 2;
(b) a polynucleotide amplified from a plant nucleic acid library using the primers of SEQ ID NOS: 3–7;
(c) a polynucleotide comprising at least 20 contiguous bases of SEQ ID NOS: 1;
(d) a polynucleotide encoding a plant WEE1 protein;
(e) a polynucleotide having at least 50% sequence identity to SEQ ID NOS: 1, wherein the % sequence identity is based on the entire sequence;
(f) a polynucleotide comprising at least 25 nucleotides in length which hybridizes under low stringency conditions to a polynucleotide having the sequence set forth in SEQ ID NO: 1, wherein the conditions include hybridization with a buffer solution of 30% formamide, 1 M NaCl, 1% SDS (sodium dodecyl sulfate) at 37° C., and a wash in 2×SSC at 50° C.
(g) a polynucleotide comprising the sequence set forth in SEQ ID NO: 1; and
(h) a polynucleotide complementary to a polynucleotide of (a) through (g).

Other aspects of the present invention include expression cassettes comprising the nucleic acid operably linked to a promoter, host cells transfected with the expression cassette, and transgenic plants and seeds comprising the expression cassette.

In a further aspect, the present invention relates to a method of modulating expression of the nucleic acids in a plant, comprising the steps of:
(a) transforming a plant cell with an expression cassette comprising a nucleic acid of the present invention operably linked to a promoter;
(b) growing the plant cell under plant growing conditions for a time sufficient to modulate expression of the nucleic acids in the plant.

Expression of the nucleic acids encoding the proteins of the present invention can be increased or decreased relative to a non-transformed control plant.

Also provided is a method for transiently modulating the level of WEE1 protein activity in plant cells comprising introducing into the plant cells a member selected from the group consisting of:

(a) at least one wee1 polynucleotide, operably linked to a promoter, wherein the polynucleotide is in sense or antisense orientation;

(b) at least one polynucleotide of claim 1, operably linked to a promoter, wherein the polynucleotide is in sense or antisense orientation;

(c) at least one wee1 RNA, wherein the RNA is in sense or antisense orientation;

(d) at least one polynucleotide of claim 1, wherein the polynucleotide is RNA in sense or antisense orientation;

(e) at least one double stranded wee1 RNA, wherein the double-stranded RNA comprises the entire span of the wee1 gene or a portion of the polynucleotide;

(f) at least one WEE1 polypeptide;

(g) at least one polypeptide of claim 12;

(h) an antibody directed against WEE1; and (i) an antisense oligonucleotide that complements and binds to its designated target sequence within the wee1 RNA.

The isolated nucleic acids of the present invention can be made using (a) standard recombinant methods, (b) synthetic techniques, or combinations thereof. In some embodiments, the polynucleotides of the present invention will be cloned, amplified, or otherwise constructed from a monocot or dicot. In preferred embodiments the monocot is corn, sorghum, barley, wheat, millet, or rice. Preferred dicots include soybeans, sunflower, canola, alfalfa, cotton, potato, or cassaya.

Functional fragments included in the invention can be obtained using primers that selectively hybridize under stringent conditions. Primers are generally at least 12 bases in length and can be as high as 200 bases, but will generally be from 15 to 75, preferably from 15 to 50. Functional fragments can be identified using a variety of techniques such as restriction analysis, Southern analysis, primer extension analysis, and DNA sequence analysis.

The present invention includes a plurality of polynucleotides that encode for the identical amino acid sequence. The degeneracy of the genetic code allows for such "silent variations" which can be used, for example, to selectively hybridize and detect allelic variants of polynucleotides of the present invention. Additionally, the present invention includes isolated nucleic acids comprising allelic variants. The term "allele" as used herein refers to a related nucleic acid of the same gene.

Variants of nucleic acids included in the invention can be obtained, for example, by oligonucleotide-directed mutagenesis, linker-scanning mutagenesis, mutagenesis using the polymerase chain reaction, and the like. See, for example, Ausubel, pages 8.0.3–8.5.9. Also, see generally, McPherson (ed.), *DIRECTED MUTAGENESIS: A Practical approach*, (IRL Press, 1991). Thus, the present invention also encompasses DNA molecules comprising nucleotide sequences that have substantial sequence similarity with the inventive sequences.

Variants included in the invention may contain individual substitutions, deletions or additions to the nucleic acid or polypeptide sequences. Such changes will alter, add or delete a single amino acid or a small percentage of amino acids in the encoded sequence. Variants are referred to as "conservatively modified variants" where the alteration results in the substitution of an amino acid with a chemically similar amino acid. When the nucleic acid is prepared or altered synthetically, advantage can be taken of known codon preferences of the intended host.

The present invention also includes "shufflents" produced by sequence shuffling of the inventive polynucleotides to obtain a desired characteristic. Sequence shuffling is described in PCT publication No. 96/19256. See also, Zhang, J. H., et al. *Proc. Natl. Acad. Sci.* USA 94:4504–4509 (1997).

The present invention also includes the use of 5' and/or 3' UTR regions for modulation of translation of heterologous coding sequences. Positive sequence motifs include translational initiation consensus sequences (Kozak, *Nucleic Acids Res.* 15:8125 (1987)) and the 7-methylguanosine cap structure (Drummond et al., *Nucleic Acids Res.* 13:7375 (1985)). Negative elements include stable intramolecular 5' UTR stem-loop structures (Muesing et al., *Cell* 48:691 (1987)) and AUG sequences or short open reading frames preceded by an appropriate AUG in the 5' UTR (Kozak, supra, Rao et al., *Mol. and Cell. Biol.* 8:284 (1988)).

Further, the polypeptide-encoding segments of the polynucleotides of the present invention can be modified to alter codon usage. Altered codon usage can be employed to alter translational efficiency and/or to optimize the coding sequence for expression in a desired host or to optimize the codon usage in a heterologous sequence for expression in maize. Codon usage in the coding regions of the polynucleotides of the present invention can be analyzed statistically using commercially available software packages such as "Codon Preference" available from the University of Wisconsin Genetics Computer Group (see Devereaux et al., *Nucleic Acids Res.* 12:387–395 (1984)) or MacVector 4.1 (Eastman Kodak Co., New Haven, Conn.).

For example, the inventive nucleic acids can be optimized for enhanced expression in organisms of interest. See, for example, EPA0359472; WO91/16432; Perlak et al. (1991) *Proc. Natl. Acad. Sci. USA* 88:3324–3328; and Murray et al. (1989) *Nucleic Acids Res.* 17:477–498. In this manner, the genes can be synthesized utilizing species-preferred codons. See, for example, Murray et al. (1989) *Nucleic Acids Res.* 17:477–498, the disclosure of which is incorporated herein by reference.

The present invention provides subsequences comprising isolated nucleic acids containing at least 16 contiguous bases of the inventive sequences. For example the isolated nucleic acid includes those comprising at least 20, 25, 30, 35, 40, 45, 50, 55, 60, 65, 70, 75, 80, 85, 90, 95, or 100 contiguous nucleotides of the inventive sequences. Subsequences of the isolated nucleic acid can be used to modulate or detect gene expression by introducing into the subsequences compounds which bind, intercalate, cleave and/or crosslink to nucleic acids.

The nucleic acids of the invention may conveniently comprise a multi-cloning site comprising one or more endonuclease restriction sites inserted into the nucleic acid to aid in isolation of the polynucleotide. Also, translatable sequences may be inserted to aid in the isolation of the translated polynucleotide of the present invention. For example, a hexa-histidine marker sequence provides a convenient means to purify the proteins of the present invention.

A polynucleotide of the present invention can be attached to a vector, adapter, promoter, transit peptide or linker for cloning and/or expression of a polynucleotide of the present invention. Additional sequences may be added to such cloning and/or expression sequences to optimize their function in cloning and/or expression, to aid in isolation of the polynucleotide, or to improve the introduction of the polynucleotide into a cell. Use of cloning vectors, expression vectors, adapters, and linkers is well known and extensively described in the art. For a description of such nucleic acids see, for example, Stratagene Cloning Systems, Catalogs 1995, 1996, 1997 (La Jolla, Calif.); and, Amersham Life Sciences, Inc, Catalog '97 (Arlington Heights, Ill.).

The isolated nucleic acid compositions of this invention, such as RNA, cDNA, genomic DNA, or a hybrid thereof, can be obtained from plant biological sources using any number of cloning methodologies known to those of skill in the art. In some embodiments, oligonucleotide probes which selectively hybridize, under stringent conditions, to the polynucleotides of the present invention are used to identify the desired sequence in a cDNA or genomic DNA library.

Exemplary total RNA and mRNA isolation protocols are described in *Plant Molecular Biology: A Laboratory Manual*, Clark, Ed., Springer-Verlag, Berlin (1997); and, *Current Protocols in Molecular Biology*, Ausubel, et al., Eds., Greene Publishing and Wiley-Interscience, New York (1995). Total RNA and mRNA isolation kits are commercially available from vendors such as Stratagene (La Jolla, Calif.), Clonetech (Palo Alto, Calif.), Pharmacia (Piscataway, N.J.), and 5'–3' (Paoli, Pa.). See also, U.S. Pat. Nos. 5,614,391; and, 5,459,253.

Typical cDNA synthesis protocols are well known to the skilled artisan and are described in such standard references as: *Plant Molecular Biology: A Laboratory Manual*, Clark, Ed., Springer-Verlag, Berlin (1997); and, *Current Protocols in Molecular Biology*, Ausubel, et al., Eds., Greene Publishing and Wiley-Interscience, New York (1995). cDNA synthesis kits are available from a variety of commercial vendors such as Stratagene or Pharmacia.

An exemplary method of constructing a greater than 95% pure full-length cDNA library is described by Carninci et al., *Genomics*, 37:327–336 (1996). Other methods for producing full-length libraries are known in the art. See, e.g., Edery et al., *Mol. Cell Biol.*, 15(6):3363–3371 (1995); and, PCT Application WO 96/34981.

It is often convenient to normalize a cDNA library to create a library in which each clone is more equally represented. A number of approaches to normalize cDNA libraries are known in the art. Construction of normalized libraries is described in Ko, *Nucl. Acids. Res.*, 18(19):5705–5711 (1990); Patanjali et al., *Proc. Natl. Acad. U.S.A.*, 88:1943–1947 (1991); U.S. Pat. Nos. 5,482,685 and 5,637,685; and Soares et al., *Proc. Natl. Acad. Sci. USA*, 91:9228–9232 (1994).

Subtracted cDNA libraries are another means to increase the proportion of less abundant cDNA species. See, Foote et al. in, *Plant Molecular Biology: A Laboratory Manual*, Clark, Ed., Springer-Verlag, Berlin (1997); Kho and Zarbl, *Technique*, 3(2):58–63 (1991); Sive and St. John, *Nucl. Acids Res.*, 16(22):10937 (1988); *Current Protocols in Molecular Biology*, Ausubel, et al., Eds., Greene Publishing and Wiley-Interscience, New York (1995); and, Swaroop et al., *Nucl. Acids Res.*, 19(8):1954 (1991). cDNA subtraction kits are commercially available. See, e.g., PCR-Select (Clontech).

To construct genomic libraries, large segments of genomic DNA are generated by random fragmentation. Examples of appropriate molecular biological techniques and instructions are found in Sambrook, et al., *Molecular Cloning: A Laboratory Manual*, 2nd Ed., Cold Spring Harbor Laboratory Vols. 1–3 (1989), Methods in Enzymology, Vol. 152: *Guide to Molecular Cloning Techniques*, Berger and Kimmel, Eds., San Diego: Academic Press, Inc. (1987), *Current Protocols in Molecular Biology*, Ausubel, et al., Eds., Greene Publishing and Wiley-Interscience, New York (1995); *Plant Molecular Biology: A Laboratory Manual*, Clark, Ed., Springer-Verlag, Berlin (1997). Kits for construction of genomic libraries are also commercially available.

The cDNA or genomic library can be screened using a probe based upon the sequence of a nucleic acid of the present invention such as those disclosed herein. Probes may be used to hybridize with genomic DNA or cDNA sequences to isolate homologous genes in the same or different plant species. Those of skill in the art will appreciate that various degrees of stringency of hybridization can be employed in the assay; and either the hybridization or the wash medium can be stringent. The degree of stringency can be controlled by temperature, ionic strength, pH and the presence of a partially denaturing solvent such as formamide.

Typically, stringent hybridization conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide.

Preferably the hybridization is conducted under low stringency conditions which include hybridization with a buffer solution of 30% formamide, 1 M NaCl, 1% SDS (sodium dodecyl sulfate) at 37° C., and a wash in 1× to 2×SSC (20×SSC=3.0 M NaCl/0.3 M trisodium citrate) at 50° C. More preferably the hybridization is conducted under moderate stringency conditions which include hybridization in 40% formamide, 1 M NaCl, 1% SDS at 37° C., and a wash in 0.5× to 1×SSC at 55° C. Most preferably the hybridization is conducted under high stringency conditions which include hybridization in 50% formamide, 1 M NaCl, 1% SDS at 37° C., and a wash in 0.1×SSC at 60° C. The time for conducting the hybridization is not critical and can be in the range of from 4 to 16 hours.

An extensive guide to the hybridization of nucleic acids is found in Tijssen, *Laboratory Techniques in Biochemistry and Molecular Biology—Hybridization with Nucleic Acid Probes*, Part I, Chapter 2 "*Overview of principles of hybridization and the strategy of nucleic acid probe assays*", Elsevier, N.Y. (1993); and *Current Protocols in Molecular Biology*, Chapter 2, Ausubel, et al., Eds., Greene Publishing and Wiley-Interscience, New York (1995). Often, cDNA libraries will be normalized to increase the representation of relatively rare cDNAs.

The nucleic acids of the invention can be amplified from nucleic acid samples using amplification techniques. For instance, polymerase chain reaction (PCR) technology can be used to amplify the sequences of polynucleotides of the present invention and related genes directly from genomic DNA or cDNA libraries. PCR and other in vitro amplification methods may also be useful, for example, to clone nucleic acid sequences that code for proteins to be expressed, to make nucleic acids to use as probes for detecting the presence of the desired mRNA in samples, for nucleic acid sequencing, or for other purposes.

Examples of techniques useful for in vitro amplification methods are found in Berger, Sambrook, and Ausubel, as well as Mullis et al., U.S. Pat. No. 4,683,202 (1987); and, *PCR Protocols A Guide to Methods and Applications*, Innis et al., Eds., Academic Press Inc., San Diego, Calif. (1990). Commercially available kits for genomic PCR amplification are known in the art. See, e.g., Advantage-GC Genomic PCR Kit (Clontech). The T4 gene 32 protein (Boehringer Mannheim) can be used to improve yield of long PCR products.

PCR-based screening methods have also been described. Wilfinger et al. describe a PCR-based method in which the longest cDNA is identified in the first step so that incomplete clones can be eliminated from study. *BioTechniques,* 22(3):481–486 (1997).

In one aspect of the invention, nucleic acids can be amplified from a plant such as *Zea mays* nucleic acid library. The nucleic acid library may be a cDNA library, a genomic library, or a library generally constructed from nuclear transcripts at any stage of intron processing.

Libraries can be made from a variety of maize tissues. Good results have been obtained using mitotically active tissues such as shoot meristems, shoot meristem cultures, embryos, callus and suspension cultures, immature ears and tassels, and young seedlings. The cDNA of the present invention was obtained from developing endosperm. Since cell cycle proteins are typically expressed at specific cell cycle stages it may be possible to enrich for such rare messages using exemplary cell cycle inhibitors such as aphidicolin, hydroxyurea, mimosine, and double-phosphate starvation methods to block cells at the G1/S boundary. Cells can also be blocked at this stage using the double phosphate starvation method. Hormone treatments that stimulate cell division, for example cytokinin, would also increase expression of the cell cycle RNA.

Alternatively, the sequences of the invention can be used to isolate corresponding sequences in other organisms, particularly other plants, more particularly, other monocots. In this manner, methods such as PCR, hybridization, and the like can be used to identify such sequences having substantial sequence similarity to the sequences of the invention. See, for example, Sambrook et al. (1989) *Molecular Cloning: A Laboratory Manual* (2d ed., Cold Spring Harbor Laboratory Press, Plainview, N.Y.) and Innis et al. (1990), *PCR Protocols: A Guide to Methods and Applications* (Academic Press, New York). Coding sequences isolated based on their sequence identity to the entire inventive coding sequences set forth herein or to fragments thereof are encompassed by the present invention.

The isolated nucleic acids of the present invention can also be prepared by direct chemical synthesis by methods such as the phosphotriester method of Narang et al., *Meth. Enzymol.* 68:90–99 (1979); the phosphodiester method of Brown et al., *Meth. Enzymol.* 68:109–151 (1979); the diethylphosphoramidite method of Beaucage et al., *Tetra. Lett.* 22:1859–1862 (1981); the solid phase phosphoramidite triester method described by Beaucage and Caruthers, *Tetra. Letts.* 22(20):1859–1862 (1981), e.g., using an automated synthesizer, e.g., as described in Needham-VanDevanter et al., *Nucleic Acids Res.*, 12:6159–6168 (1984); and, the solid support method of U.S. Pat. No. 4,458,066. Chemical synthesis generally produces a single stranded oligonucleotide. This may be converted into double stranded DNA by hybridization with a complementary sequence, or by polymerization with a DNA polymerase using the single strand as a template. One of skill will recognize that while chemical synthesis of DNA is limited to sequences of about 100 bases, longer sequences may be obtained by the ligation of shorter sequences.

Expression Cassettes

In another embodiment expression cassettes comprising isolated nucleic acids of the present invention are provided. An expression cassette will typically comprise a polynucleotide of the present invention operably linked to transcriptional initiation regulatory sequences which will direct the transcription of the polynucleotide in the intended host cell, such as tissues of a transformed plant.

The construction of expression cassettes that can be employed in conjunction with the present invention is well known to those of skill in the art in light of the present disclosure. See, e.g., Sambrook, et al.; *Molecular Cloning: A Laboratory Manual*; Cold Spring Harbor, N.Y.; (1989); Gelvin, et al.; *Plant Molecular Biology Manual*; (1990); *Plant Biotechnology: Commercial Prospects and Problems*, eds. Prakash, et al.; Oxford & IBH Publishing Co.; New Delhi, India; (1993); and Heslot, et al.; *Molecular Biology and Genetic Engineering of Yeasts*; CRC Press, Inc., USA; (1992); each incorporated herein in its entirety by reference.

For example, plant expression vectors may include (1) a cloned plant nucleic acid under the transcriptional control of 5' and 3' regulatory sequences and (2) a dominant selectable marker. Such plant expression vectors may also contain, if desired, a promoter regulatory region (e.g., one conferring inducible, constitutive, environmentally- or developmentally-regulated, or cell- or tissue-specific/selective expression), a transcription initiation start site, a ribosome binding site, an RNA processing signal, a transcription termination site, and/or a polyadenylation signal.

Constitutive, tissue-preferred or inducible promoters can be employed. Examples of constitutive promoters include the cauliflower mosaic virus (CaMV) 35S transcription initiation region, the 1'- or 2'-promoter derived from T-DNA of *Agrobacterium tumefaciens*, the ubiquitin 1 promoter, the Smas promoter, the cinnamyl alcohol dehydrogenase promoter (U.S. Pat. No. 5,683,439), the Nos promoter, the pEmu promoter, the rubisco promoter, the GRP1-8 promoter and other transcription initiation regions from various plant genes known to those of skill.

Examples of inducible promoters are the Adh1 promoter which is inducible by hypoxia or cold stress, the Hsp70 promoter which is inducible by heat stress, and the PPDK promoter which is inducible by light. Also useful are promoters which are chemically inducible.

Examples of promoters under developmental control include promoters that initiate transcription preferentially in certain tissues, such as leaves, roots, fruit, seeds, or flowers. An exemplary promoter is the anther specific promoter 5126 (U.S. Pat. Nos. 5,689,049 and 5,689,051). Examples of seed-preferred promoters include, but are not limited to, phaseolin, 27 kD gamma zein promoter and waxy promoter, Boronat, A., Martinez, M. C., Reina, M., Puigdomenech, P. and Palau, J.; Isolation and sequencing of a 28 kD glutelin-2 gene from maize: Common elements in the 5' flanking regions among zein and glutelin genes; *Plant Sci.* 47, 95–102 (1986) and Reina, M., Ponte, I., Guillen, P., Boronat, A. and Palau, J., Sequence analysis of a genomic clone encoding a Zc2 protein from *Zea mays* W64 A, *Nucleic Acids Res.* 18 (21), 6426 (1990). See the following site relating to the waxy promoter: Kloesgen, R. B., Gierl, A., Schwarz-Sommer, Z. S. and Saedler, H., Molecular analysis of the waxy locus of *Zea mays*, *Mol. Gen. Genet.* 203, 237–244 (1986). Promoters that express in the embryo, pericarp, and endosperm are disclosed in U.S. applications Ser. Nos. 60/097,233 filed Aug. 20, 1998 and 60/098,230 filed Aug. 28, 1998. The disclosures each of these are incorporated herein by reference in their entirety.

Either heterologous or non-heterologous (i.e., endogenous) promoters can be employed to direct expression of the nucleic acids of the present invention. These promoters can also be used, for example, in expression cassettes to drive expression of antisense nucleic acids to reduce, increase, or alter concentration and/or composition of the proteins of the present invention in a desired tissue.

If polypeptide expression is desired, it is generally desirable to include a polyadenylation region at the 3'-end of a polynucleotide coding region. The polyadenylation region can be derived from the natural gene, from a variety of other plant genes, or from T-DNA. The 3' end sequence to be added can be derived from, for example, the nopaline synthase or octopine synthase genes, or alternatively from another plant gene, or less preferably from any other eukaryotic gene.

An intron sequence can be added to the 5' untranslated region or the coding sequence of the partial coding sequence to increase the amount of the mature message that accumulates. See for example Buchman and Berg, Mol. Cell Biol. 8:4395–4405(1988); Callis et al., Genes Dev. 1:1183–1200 (1987). Use of maize introns Adh1-S intron 1, 2, and 6, the Bronze-1 intron are known in the art. See generally, The Maize Handbook, Chapter 116, Freeling and Walbot, Eds., Springer, N.Y. (1994).

The vector comprising the sequences from a polynucleotide of the present invention will typically comprise a marker gene which confers a selectable phenotype on plant cells. Usually, the selectable marker gene will encode antibiotic or herbicide resistance. Suitable genes include those coding for resistance to the antibiotic spectinomycin or streptomycin (e.g., the aada gene), the streptomycin phosphotransferase (SPT) gene coding for streptomycin resistance, the neomycin phosphotransferase (NPTII) gene encoding kanamycin or geneticin resistance, the hygromycin phosphotransferase (HPT) gene coding for hygromycin resistance.

Suitable genes coding for resistance to herbicides include those which act to inhibit the action of acetolactate synthase (ALS), in particular the sulfonylurea-type herbicides (e.g., the acetolactate synthase (ALS) gene containing mutations leading to such resistance in particular the S4 and/or Hra mutations), those which act to inhibit action of glutamine synthase, such as phosphinothricin or basta (e.g., the bar gene), or other such genes known in the art. The bar gene encodes resistance to the herbicide basta and the ALS gene encodes resistance to the herbicide chlorsulfuron.

Typical vectors useful for expression of nucleic acids in higher plants are well known in the art and include vectors derived from the tumor-inducing (Ti) plasmid of *Agrobacterium tumefaciens* described by Rogers et al., Meth. In Enzymol., 153:253–277 (1987). Exemplary *A. tumefaciens* vectors useful herein are plasmids pKYLX6 and pKYLX7 of Schardl et al., Gene, 61:1–11 (1987) and Berger et al., Proc. Natl. Acad. Sci. U.S.A., 86:8402–8406 (1989). Another useful vector herein is plasmid pBI101.2 that is available from Clontech Laboratories, Inc. (Palo Alto, Calif.).

A variety of plant viruses that can be employed as vectors are known in the art and include cauliflower mosaic virus (CaMV), geminivirus, brome mosaic virus, and tobacco mosaic virus.

A polynucleotide of the present invention can be expressed in either sense or anti-sense orientation as desired. In plant cells, it has been shown that antisense RNA inhibits gene expression by preventing the accumulation of mRNA which encodes the enzyme of interest, see, e.g., Sheehy et al., Proc. Nat'l. Acad. Sci. (USA) 85:8805–8809 (1988); and Hiatt et al., U.S. Pat. No. 4,801,340.

Another method of suppression is sense suppression. Introduction of nucleic acid configured in the sense orientation has been shown to be an effective means by which to block the transcription of target genes. For an example of the use of this method to modulate expression of endogenous genes see, Napoli et al., The Plant Cell 2: 279–289 (1990) and U.S. Pat. No. 5,034,323.

A method of down-regulation of the protein involves using PEST sequences that provide a target for degradation of the protein.

Catalytic RNA molecules or ribozymes can also be used to inhibit expression of plant genes. The inclusion of ribozyme sequences within antisense RNAs confers RNA-cleaving activity upon them, thereby increasing the activity of the constructs. The design and use of target RNA-specific ribozymes is described in Haseloff et al., Nature 334:585–591 (1988).

A variety of cross-linking agents, alkylating agents and radical generating species as pendant groups on polynucleotides of the present invention can be used to bind, label, detect, and/or cleave nucleic acids. For example, Vlassov, V. V., et al., Nucleic Acids Res (1986) 14:4065–4076, describe covalent bonding of a single-stranded DNA fragment with alkylating derivatives of nucleotides complementary to target sequences. A report of similar work by the same group is that by Knorre, D. G., et al., Biochimie (1985) 67:785–789. Iverson and Dervan also showed sequence-specific cleavage of single-stranded DNA mediated by incorporation of a modified nucleotide which was capable of activating cleavage (J Am Chem Soc (1987) 109:1241–1243). Meyer, R. B., et al., J Am Chem Soc (1989) 111:8517–8519, effect covalent crosslinking to a target nucleotide using an alkylating agent complementary to the single-stranded target nucleotide sequence. A photoactivated crosslinking to single-stranded oligonucleotides mediated by psoralen was disclosed by Lee, B. L., et al., Biochemistry (1988) 27:3197–3203. Use of crosslinking in triple-helix forming probes was also disclosed by Home, et al., J Am Chem Soc (1990) 112:2435–2437. Use of N4, N4-ethanocytosine as an alkylating agent to crosslink to single-stranded oligonucleotides has also been described by Webb and Matteucci, J Am Chem Soc (1986) 108:2764–2765; Nucleic Acids Res (1986) 14:7661–7674; Feteritz et al., J. Am. Chem. Soc. 113:4000 (1991). Various compounds to bind, detect, label, and/or cleave nucleic acids are known in the art. See, for example, U.S. Pat. Nos. 5,543,507; 5,672,593; 5,484,908; 5,256,648; and, 5,681,941.

Proteins

Also provided is an isolated protein comprising a member selected from the group consisting of:

(a) a polypeptide comprising at least 25 contiguous amino acids of SEQ ID NO: 2;

(b) a polypeptide which is a plant WEE1 protein;

(c) a polypeptide comprising at least 55% sequence identity to SEQ ID NO: 2, wherein the % sequence identity is based on the entire sequence;

(d) a polypeptide encoded by a nucleic acid of claim 1; and (e) a polypeptide characterized by SEQ ID NO: 2.

Proteins of the present invention include proteins derived from the native protein by deletion (so-called truncation), addition or substitution of one or more amino acids at one or more sites in the native protein. Such variants may result from, for example, genetic polymorphism or from human manipulation. Methods for such manipulations are generally known in the art.

For example, amino acid sequence variants of the polypeptide can be prepared by mutations in the cloned DNA sequence encoding the native protein of interest. Methods for mutagenesis and nucleotide sequence alterations are well known in the art. See, for example, Walker and Gaastra, eds. (1983) *Techniques in Molecular Biology* (MacMillan Publishing Company, New York); Kunkel (1985) *Proc. Natl. Acad. Sci. USA* 82:488–492; Kunkel et al. (1987) *Methods Enzymol.* 154:367–382; Sambrook et al. (1989) *Molecular Cloning: A Laboratory Manual* (Cold Spring Harbor, N.Y.); U.S. Pat. No. 4,873,192; and the references cited therein; herein incorporated by reference. Guidance as to appropriate amino acid substitutions that do not affect biological activity of the protein of interest may be found in the model of Dayhoff et al. (1978) *Atlas of Protein Sequence and Structure* (Natl. Biomed. Res. Found., Washington, D.C.), herein incorporated by reference. Conservative substitutions, such as exchanging one amino acid with another having similar properties, may be preferred.

In constructing variants of the proteins of interest, modifications to the nucleotide sequences encoding the variants will be made such that variants continue to possess the desired activity. Obviously, any mutations made in the DNA encoding the variant protein must not place the sequence out of reading frame and preferably will not create complementary regions that could produce secondary mRNA structure. See EP Patent Application Publication No. 75,444.

The isolated proteins of the present invention include a polypeptide comprising at least 23 contiguous amino acids encoded by any one of the nucleic acids of the present invention, or polypeptides which are conservatively modified variants thereof. The proteins of the present invention or variants thereof can comprise any number of contiguous amino acid residues from a polypeptide of the present invention, wherein that number is selected from the group of integers consisting of from 23 to the number of residues in a full-length polypeptide of the present invention. Optionally, this subsequence of contiguous amino acids is at least 25, 30, 35, or 40 amino acids in length, often at least 50, 60, 70, 80, or 90 amino acids in length.

The present invention includes catalytically active polypeptides (i.e., enzymes). Catalytically active polypeptides will generally have a specific activity of at least 20%, 30%, or 40%, and preferably at least 50%, 60%, or 70%, and most preferably at least 80%, 90%, or 95% that of the native (non-synthetic), endogenous polypeptide. Further, the substrate specificity ($k_{cat}/K_m$) is optionally substantially similar to the native (non-synthetic), endogenous polypeptide. Typically, the $K_m$ will be at least 30%, 40%, or 50%, that of the native (non-synthetic), endogenous polypeptide; and more preferably at least 60%, 70%, 80%, or 90%. Methods of assaying and quantifying measures of enzymatic activity and substrate specificity ($k_{cat}/K_m$), are well known to those of skill in the art.

The present invention includes modifications that can be made to an inventive protein without diminishing its biological activity. Some modifications may be made to facilitate the cloning, expression, or incorporation of the targeting molecule into a fusion protein. Such modifications are well known to those of skill in the art and include, for example, a methionine added at the amino terminus to provide an initiation site, or additional amino acids (e.g., poly His) placed on either terminus to create conveniently located restriction sites or termination codons or purification sequences.

A protein of the present invention can be expressed in a recombinantly engineered cell such as bacteria, yeast, insect, mammalian, or preferably plant cells. The cells produce the protein in a non-natural condition (e.g., in quantity, composition, location, and/or time), because they have been genetically altered through human intervention to do so.

Typically, an intermediate host cell will be used in the practice of this invention to increase the copy number of the cloning vector. With an increased copy number, the vector containing the nucleic acid of interest can be isolated in significant quantities for introduction into the desired plant cells.

Host cells that can be used in the practice of this invention include prokaryotes, including bacterial hosts such as *Escherichia coli, Salmonella typhimurium*, and *Serratia marcescens*. Eukaryotic hosts such as yeast or filamentous fungi may also be used in this invention. It preferred to use plant promoters that do not cause expression of the polypeptide in bacteria.

Commonly used prokaryotic control sequences include promoters such as the beta lactamase (penicillinase) and lactose (lac) promoter systems (Chang et al., Nature 198:1056 (1977)), the tryptophan (trp) promoter system (Goeddel et al., *Nucleic Acids Res.* 8:4057 (1980)) and the lambda derived P L promoter and N-gene ribosome binding site (Shimatake et al., Nature 292:128 (1981)). The inclusion of selection markers in DNA vectors transfected in *E. coli* is also useful. Examples of such markers include genes specifying resistance to ampicillin, tetracycline, or chloramphenicol.

The vector is selected to allow introduction into the appropriate host cell. Bacterial vectors are typically of plasmid or phage origin. Expression systems for expressing a protein of the present invention are available using Bacillus sp. and Salmonella (Palva, et al., *Gene* 22: 229–235 (1983); Mosbach, et al., *Nature* 302: 543–545 (1983)).

Synthesis of heterologous proteins in yeast is well known. See Sherman, F., et al., *Methods in Yeast Genetics*, Cold Spring Harbor Laboratory (1982). Two widely utilized yeast for production of eukaryotic proteins are *Saccharomyces cerevisiae* and *Pichia pastors*. Vectors, strains, and protocols for expression in Saccharomyces and Pichia are known in the art and available from commercial suppliers (e.g., Invitrogen). Suitable vectors usually have expression control sequences, such as promoters, including 3-phosphoglycerate kinase or alcohol oxidase, and an origin of replication, termination sequences and the like as desired.

A protein of the present invention, once expressed, can be isolated from yeast by lysing the cells and applying standard protein isolation techniques to the lysates. The monitoring of the purification process can be accomplished by using Western blot techniques or radioimmunoassay of other standard immunoassay techniques.

The proteins of the present invention can also be constructed using non-cellular synthetic methods. Solid phase synthesis of proteins of less than about 50 amino acids in length may be accomplished by attaching the C-terminal amino acid of the sequence to an insoluble support followed by sequential addition of the remaining amino acids in the sequence. Techniques for solid phase synthesis are described by Barany and Merrifield, Solid-Phase Peptide Synthesis, pp. 3–284 in *The Peptides: Analysis, Synthesis, Biology. Vol. 2: Special Methods in Peptide Synthesis, Part A*.; Merrifield, et al., *J. Am. Chem. Soc.* 85:2149–2156 (1963), and Stewart et al., *Solid Phase Peptide Synthesis*, 2nd ed., Pierce Chem. Co., Rockford, Ill. (1984). Proteins of greater length may be synthesized by condensation of the amino and carboxy termini of shorter fragments. Methods of forming peptide bonds by activation of a carboxy terminal end (e.g., by the use of the coupling reagent N,N'-dicyclohexylcarbodiimide) is known to those of skill.

The proteins of this invention may be purified to substantial purity by standard techniques well known in the art, including detergent solubilization, selective precipitation with such substances as ammonium sulfate, column chromatography, immunopurification methods, and others. See, for instance, R. Scopes, *Protein Purification: Principles and Practice*, Springer-Verlag: New York (1982); Deutscher, *Guide to Protein Purification*, Academic Press (1990). For example, antibodies may be raised to the proteins as described herein. Purification from *E. coli* can be achieved following procedures described in U.S. Pat. No. 4,511,503. Detection of the expressed protein is achieved by methods known in the art and include, for example, radioimmunoassays, Western blotting techniques or immunoprecipitation.

The present invention further provides a method for modulating (i.e., increasing or decreasing) the concentration or composition of the polypeptides of the present invention in a plant or part thereof. Modulation of the polypeptides can be effected by increasing or decreasing the concentration and/or the composition of the polypeptides in a plant. The method comprises transforming a plant cell with an expression cassette comprising a polynucleotide of the present invention to obtain a transformed plant cell, growing the transformed plant cell under plant forming conditions, and inducing expression of the polynucleotide in the plant for a time sufficient to modulate concentration and/or composition of the polypeptides in the plant or plant part.

In some embodiments, the content and/or composition of polypeptides of the present invention in a plant may be modulated by altering, in vivo or in vitro, the promoter of a non-isolated gene of the present invention to up- or down-regulate gene expression. In some embodiments, the coding regions of native genes of the present invention can be altered via substitution, addition, insertion, or deletion to decrease activity of the encoded enzyme. See, e.g., Kmiec, U.S. Pat. No. 5,565,350; Zarling et al., PCT/US93/03868.

In particular, modulating cell cycle proteins are expected to provide a positive growth advantage and increase crop yield. Cell cycle nucleic acids can be adducted to a second nucleic acid sequence encoding a DNA-binding domain, for use in two-hybrid systems to identify WEE1-interacting proteins. It is expected that modulating the level of cell cycle protein, i.e. overexpression of wee1 in conjunction with overexpression of G1/S phase-transition stimulating genes, will increase endoreduplication. Abrogation of WEE1 activity is expected to derepress the cyclin dependant kinases. Abrogation of WEE1 activity is also expected to shorten the G2 phase of the mitotic cycle. Increased endoreduplication is expected to increase cell size, the size of the seed, the size of the endosperm and the amount of protein in the seed.

In some embodiments, an isolated nucleic acid (e.g., a vector) comprising a promoter sequence is transfected into a plant cell. Subsequently, a plant cell comprising the isolated nucleic acid is selected for by means known to those of skill in the art such as, but not limited to, Southern blot, DNA sequencing, or PCR analysis using primers specific to the promoter and to the nucleic acid and detecting amplicons produced therefrom. A plant or plant part altered or modified by the foregoing embodiments is grown under plant forming conditions for a time sufficient to modulate the concentration and/or composition of polypeptides of the present invention in the plant. Plant forming conditions are well known in the art.

In general, concentration of the polypeptides is increased or decreased by at least 5%, 10%, 20%, 30%, 40%, 50%, 60%, 70%, 80%, or 90% relative to a native control plant, plant part, or cell lacking the aforementioned expression cassette. Modulation in the present invention may occur during and/or subsequent to growth of the plant to the desired stage of development.

Modulating nucleic acid expression temporally and/or in particular tissues can be controlled by employing the appropriate promoter operably linked to a polynucleotide of the present invention in, for example, sense or antisense orientation as discussed in greater detail above. Induction of expression of a polynucleotide of the present invention can also be controlled by exogenous administration of an effective amount of inducing compound. Inducible promoters and inducing compounds that activate expression from these promoters are well known in the art.

In preferred embodiments, the polypeptides of the present invention are modulated in monocots or dicots, preferably corn, soybean, sunflower, sorghum, canola, wheat, alfalfa, cotton, rice, barley and millet.

Means of detecting the proteins of the present invention are not critical aspects of the present invention. In a preferred embodiment, the proteins are detected and/or quantified using any of a number of well recognized immunological binding assays (see, e.g., U.S. Pat. Nos. 4,366,241; 4,376,110; 4,517,288; and 4,837,168). For a review of the general immunoassays, see also Methods in Cell Biology, Vol. 37: *Antibodies in Cell Biology*, Asai, Ed., Academic Press, Inc. New York (1993); *Basic and Clinical Immunology* 7th Edition, Stites & Terr, Eds. (1991). Moreover, the immunoassays of the present invention can be performed in any of several configurations, e.g., those reviewed in *Enzyme Immunoassay*, Maggio, Ed., CRC Press, Boca Raton, Fla. (1980); Tijan, Practice and Theory of Enzyme Immunoassays, *Laboratory Techniques in Biochemistry and Molecular Biology*, Elsevier Science Publishers B.V., Amsterdam (1985); Harlow and Lane, supra; *Immunoassay: A Practical Guide*, Chan, Ed., Academic Press, Orlando, Fla. (1987); *Principles and Practice of Immunoassays*, Price and Newman Eds., Stockton Press, NY (1991); and *Non-isotopic Immunoassays*, Ngo, Ed., Plenum Press, NY (1988).

Typical methods for detecting proteins include Western blot (immunoblot) analysis, analytic biochemical methods such as electrophoresis, capillary electrophoresis, high performance liquid chromatography (HPLC), thin layer chromatography (TLC), hyperdiffusion chromatography, and the like, and various immunological methods such as fluid or gel precipitation reactions, immunodiffusion (single or double), immunoelectrophoresis, radioimmunoassays (RIAs), enzyme-linked immunosorbent assays (ELISAs), immunofluorescent assays, and the like.

Non-radioactive labels are often attached by indirect means. Generally, a ligand molecule (e.g., biotin) is covalently bound to the molecule. The ligand then binds to an anti-ligand (e.g., streptavidin) molecule which is either inherently detectable or covalently bound to a signal system, such as a detectable enzyme, a fluorescent compound, or a chemiluminescent compound. A number of ligands and anti-ligands can be used. Where a ligand has a natural anti-ligand, for example, biotin, thyroxine, and cortisol, it can be used in conjunction with the labeled, naturally occurring anti-ligands. Alternatively, any haptenic or antigenic compound can be used in combination with an antibody.

The molecules can also be conjugated directly to signal generating compounds, e.g., by conjugation with an enzyme or fluorophore. Enzymes of interest as labels will primarily be hydrolases, particularly phosphatases, esterases and glycosidases, or oxidoreductases, particularly peroxidases. Fluorescent compounds include fluorescein and its derivatives, rhodamine and its derivatives, dansyl, umbelliferone, etc. Chemiluminescent compounds include luciferin, and 2,3-dihydrophthalazinediones, e.g., luminol. For a review of various labeling or signal producing systems which may be used, see, U.S. Pat. No. 4,391,904, which is incorporated herein by reference.

Some assay formats do not require the use of labeled components. For instance, agglutination assays can be used to detect the presence of the target antibodies. In this case, antigen-coated particles are agglutinated by samples comprising the target antibodies. In this format, none of the components need be labeled and the presence of the target antibody is detected by simple visual inspection.

The proteins of the present invention can be used for identifying compounds that bind to (e.g., substrates), and/or increase or decrease (i.e., modulate) the enzymatic activity of, catalytically active polypeptides of the present invention. The method comprises contacting a polypeptide of the present invention with a compound whose ability to bind to or modulate enzyme activity is to be determined. The polypeptide employed will have at least 20%, preferably at least 30% or 40%, more preferably at least 50% or 60%, and most preferably at least 70% or 80% of the specific activity of the native, full-length polypeptide of the present invention (e.g., enzyme). Methods of measuring enzyme kinetics are well known in the art. See, e.g., Segel, *Biochemical Calculations*, 2$^{nd}$ ed., John Wiley and Sons, New York (1976).

Antibodies can be raised to a protein of the present invention, including individual, allelic, strain, or species variants, and fragments thereof, both in their naturally occurring (full-length) forms and in recombinant forms. Additionally, antibodies are raised to these proteins in either their native configurations or in non-native configurations. Anti-idiotypic antibodies can also be generated. Many methods of making antibodies are known to persons of skill.

In some instances, it is desirable to prepare monoclonal antibodies from various mammalian hosts, such as mice, rodents, primates, humans, etc. Description of techniques for preparing such monoclonal antibodies are found in, e.g., *Basic and Clinical Immunology*, 4th ed., Stites et al., Eds., Lange Medical Publications, Los Altos, Calif., and references cited therein; Harlow and Lane, Supra; Goding, *Monoclonal Antibodies: Principles and Practice*, 2nd ed., Academic Press, New York, N.Y. (1986); and Kohler and Milstein, *Nature* 256: 495–497 (1975).

Other suitable techniques involve selection of libraries of recombinant antibodies in phage or similar vectors (see, e.g., Huse et al., *Science* 246:1275–1281 (1989); and Ward, et al., *Nature* 341:544–546 (1989); and Vaughan et al., *Nature Biotechnology*, 14:309–314 (1996)). Alternatively, high avidity human monoclonal antibodies can be obtained from transgenic mice comprising fragments of the unrearranged human heavy and light chain Ig loci (i.e., minilocus transgenic mice). Fishwild et al., *Nature Biotech.*, 14:845–851 (1996). Also, recombinant immunoglobulins may be produced. See Cabilly, U.S. Pat. No. 4,816,567; and Queen et al., *Proc. Nat'l Acad. Sci.* 86:10029–10033 (1989).

The antibodies of this invention can be used for affinity chromatography in isolating proteins of the present invention, for screening expression libraries for particular expression products such as normal or abnormal protein or for raising anti-idiotypic antibodies which are useful for detecting or diagnosing various pathological conditions related to the presence of the respective antigens.

Frequently, the proteins and antibodies of the present invention will be labeled by joining, either covalently or non-covalently, a substance which provides for a detectable signal. A wide variety of labels and conjugation techniques are known and are reported extensively in both the scientific and patent literature. Suitable labels include radionucleotides, enzymes, substrates, cofactors, inhibitors, fluorescent moieties, chemiluminescent moieties, magnetic particles, and the like.

Transfection/Transformation of Cells

The method of transformation/transfection is not critical to the invention; various methods of transformation or transfection are currently available. As newer methods are available to transform crops or other host cells they may be directly applied. Accordingly, a wide variety of methods have been developed to insert a DNA sequence into the genome of a host cell to obtain the transcription and/or translation of the sequence to effect phenotypic changes in the organism. Thus, any method that provides for efficient transformation/transfection may be employed.

A DNA sequence coding for the desired polynucleotide of the present invention, for example a cDNA, RNA or a genomic sequence, will be used to construct an expression cassette that can be introduced into the desired plant. Isolated nucleic acid acids of the present invention can be introduced into plants according techniques known in the art. Generally, expression cassettes as described above and suitable for transformation of plant cells are prepared.

Techniques for transforming a wide variety of higher plant species are well known and described in the technical, scientific, and patent literature. See, for example, Weising et al., *Ann. Rev. Genet*. 22:421–477 (1988). For example, the DNA construct may be introduced directly into the genomic DNA of the plant cell using techniques such as electroporation, PEG-mediated transfection, particle bombardment, silicon fiber delivery, or microinjection of plant cell protoplasts or embryogenic callus. See, e.g., Tomes, et al., Direct DNA Transfer into Intact Plant Cells Via Microprojectile Bombardment. pp. 197–213 in Plant Cell, Tissue and Organ Culture, Fundamental Methods. eds. O. L. Gamborg and G. C. Phillips. Springer-Verlag Berlin Heidelberg N.Y., 1995. Alternatively, the DNA constructs may be combined with suitable T-DNA flanking regions and introduced into a conventional *Agrobacterium tumefaciens* host vector. The virulence functions of the *Agrobacterium tumefaciens* host will direct the insertion of the construct and adjacent marker into the plant cell DNA when the cell is infected by the bacteria. See, U.S. Pat. No. 5,591,616.

The introduction of DNA constructs using polyethylene glycol precipitation is described in Paszkowski et al., *Embo J*. 3:2717–2722 (1984). Electroporation techniques are described in Fromm et al., *Proc. Natl. Acad. Sci.* 82:5824 (1985). Ballistic transformation techniques are described in Klein et al., *Nature* 327:70–73 (1987).

*Agrobacterium tumefaciens*-meditated transformation techniques are described in the scientific literature. See, for example Horsch et al., *Science* 233:496–498 (1984), and Fraley et al., *Proc. Natl. Acad. Sci.* 80:4803 (1983). Agrobacterium transformation of soybean cells is described in U.S. Pat. No. 5,563,055. For instance, Agrobacterium transformation of maize is described in U.S. Pat. No. 5,981,840. Agrobacterium transformation of sorghum is described in WO 98/49332. Agrobacterium transformation of Alfalfa is described in U.S. Pat. No. 5,324,646.

Other methods of transfection or transformation include (1) *Agrobacterium rhizogenes*-mediated transformation (see, e.g., Lichtenstein and Fuller In: Genetic Engineering, vol. 6, P W J Rigby, Ed., London, Academic Press, 1987; and Lichtenstein, C. P., and Draper, J. In: DNA Cloning, Vol. II, D. M. Glover, Ed., Oxford, IRI Press, 1985), Application PCT/US87/02512 (WO 88/02405 published Apr. 7, 1988) describes the use of *A. rhizogenes* strain A4 and its Ri plasmid along with *A. tumefaciens* vectors pARC8 or pARC16 (2) liposome-mediated DNA uptake (see, e.g., Freeman et al., Plant Cell Physiol. 25:1353, 1984), (3) the vortexing method (see, e.g., Kindle, *Proc. Natl. Acad. Sci., USA* 87:1228, (1990).

DNA can also be introduced into plants by direct DNA transfer into pollen as described by Zhou et al., Methods in Enzymology, 101:433 (1983); D. Hess, Intern Rev. Cytol., 107:367 (1987); Luo et al., Plane Mol. Biol. Reporter, 6:165 (1988). Expression of polypeptide coding nucleic acids can be obtained by injection of the DNA into reproductive organs of a plant as described by Pena et al., Nature, 325:274 (1987). DNA can also be injected directly into the cells of immature embryos and the rehydration of desiccated embryos as described by Neuhaus et al., Theor. Appl. Genet., 75:30 (1987); and Benbrook et al., in Proceedings Bio Expo 1986, Butterworth, Stoneham, Mass., pp. 27–54 (1986).

Animal and lower eukaryotic (e.g., yeast) host cells are competent or rendered competent for transfection by various means. There are several well-known methods of introducing DNA into animal cells. These include: calcium phosphate precipitation, fusion of the recipient cells with bacterial protoplasts containing the DNA, treatment of the recipient cells with liposomes containing the DNA, DEAE dextran, electroporation, biolistics, and micro-injection of the DNA directly into the cells. The transfected cells are cultured by means well known in the art. Kuchler, R. J., *Biochemical Methods in Cell Culture and Virology*, Dowden, Hutchinson and Ross, Inc. (1977).

Transgenic Plant Regeneration

Transformed plant cells which are derived by any of the above transformation techniques can be cultured to regenerate a whole plant which possesses the transformed genotype. Such regeneration techniques often rely on manipulation of certain phytohormones in a tissue culture growth medium, typically relying on a biocide and/or herbicide marker which has been introduced together with a polynucleotide of the present invention. For transformation and regeneration of maize see, Gordon-Kamm et al., *The Plant Cell*, 2:603–618 (1990).

Plants cells transformed with a plant expression vector can be regenerated, e.g., from single cells, callus tissue or leaf discs according to standard plant tissue culture techniques. It is well known in the art that various cells, tissues, and organs from almost any plant can be successfully cultured to regenerate an entire plant. Plant regeneration from cultured protoplasts is described in Evans et al., *Protoplasts Isolation and Culture, Handbook of Plant Cell Culture*, Macmillan Publishing Company, New York, pp. 124–176 (1983); and Binding, *Regeneration of Plants, Plant Protoplasts*, CRC Press, Boca Raton, pp. 21–73 (1985).

The regeneration of plants containing the foreign gene introduced by Agrobacterium can be achieved as described by Horsch et al., *Science*, 227:1229–1231 (1985) and Fraley et al., *Proc. Natl. Acad. Sci. U.S.A.*, 80:4803 (1983). This procedure typically produces shoots within two to four weeks and these transformant shoots are then transferred to an appropriate root-inducing medium containing the selective agent and an antibiotic to prevent bacterial growth. Transgenic plants of the present invention may be fertile or sterile.

Regeneration can also be obtained from plant callus, explants, organs, or parts thereof. Such regeneration techniques are described generally in Klee et al., *Ann. Rev. of Plant Phys.* 38:467–486 (1987). The regeneration of plants from either single plant protoplasts or various explants is well known in the art. See, for example, Methods for Plant Molecular Biology, A. Weissbach and H. Weissbach, eds., Academic Press, Inc., San Diego, Calif. (1988). For maize cell culture and regeneration see generally, *The Maize Handbook*, Freeling and Walbot, Eds., Springer, N.Y. (1994); *Corn and Corn Improvement*, $3^{rd}$ edition, Sprague and Dudley Eds., American Society of Agronomy, Madison, Wis. (1988).

One of skill will recognize that after the expression cassette is stably incorporated in transgenic plants and confirmed to be operable, it can be introduced into other plants by sexual crossing. Any of a number of standard breeding techniques can be used, depending upon the species to be crossed.

In vegetatively propagated crops, mature transgenic plants can be propagated by the taking of cuttings or by tissue culture techniques to produce multiple identical plants. Selection of desirable transgenics is made and new varieties are obtained and propagated vegetatively for commercial use. In seed propagated crops, mature transgenic plants can be self crossed to produce a homozygous inbred plant. The inbred plant produces seed containing the newly introduced heterologous nucleic acid. These seeds can be grown to produce plants that would produce the selected phenotype.

Parts obtained from the regenerated plant, such as flowers, seeds, leaves, branches, fruit, and the like are included in the invention, provided that these parts comprise cells comprising the isolated nucleic acid of the present invention. Progeny and variants, and mutants of the regenerated plants are also included within the scope of the invention, provided that these parts comprise the introduced nucleic acid sequences.

Transgenic plants expressing a selectable marker can be screened for transmission of the nucleic acid of the present invention by, for example, standard immunoblot and DNA detection techniques. Transgenic lines are also typically evaluated on levels of expression of the heterologous nucleic acid. Expression at the RNA level can be determined initially to identify and quantitate expression-positive plants. Standard techniques for RNA analysis can be employed and include PCR amplification assays using oligonucleotide primers designed to amplify only the heterologous RNA templates and solution hybridization assays using heterologous nucleic acid-specific probes. The RNA-positive plants can then analyzed for protein expression by Western immunoblot analysis using the specifically reactive antibodies of the present invention. In addition, in situ hybridization and immunocytochemistry according to standard protocols can be done using heterologous nucleic acid specific polynucleotide probes and antibodies, respectively, to localize sites of expression within transgenic tissue. Generally, a number of transgenic lines are usually screened for the incorporated nucleic acid to identify and select plants with the most appropriate expression profiles.

A preferred embodiment is a transgenic plant that is homozygous for the added heterologous nucleic acid; i.e., a transgenic plant that contains two added nucleic acid sequences, one gene at the same locus on each chromosome of a chromosome pair. A homozygous transgenic plant can be obtained by sexually mating (selfing) a heterozygous transgenic plant that contains a single added heterologous nucleic acid, germinating some of the seed produced and analyzing the resulting plants produced for altered expression of a polynucleotide of the present invention relative to a control plant (i.e., native, non-transgenic). Back-crossing to a parental plant and out-crossing with a non-transgenic plant are also contemplated.

The present invention provides a method of genotyping a plant comprising a polynucleotide of the present invention. Genotyping provides a means of distinguishing homologs of a chromosome pair and can be used to differentiate segregants in a plant population. Molecular marker methods can be used for phylogenetic studies, characterizing genetic relationships among crop varieties, identifying crosses or somatic hybrids, localizing chromosomal segments affecting monogenic traits, map based cloning, and the study of quantitative inheritance. See, e.g., *Plant Molecular Biology. A Laboratory Manual*, Chapter 7, Clark, Ed., Springer-Verlag, Berlin (1997). For molecular marker methods, see generally, The DNA Revolution by Andrew H. Paterson 1996 (Chapter 2) in: Genome Mapping in Plants (ed. Andrew H. Paterson) by Academic Press/R. G. Landis Company, Austin, Tex., pp. 7–21.

The particular method of genotyping in the present invention may employ any number of molecular marker analytic techniques such as, but not limited to, restriction fragment length polymorphisms (RFLPs). RFLPs are the product of allelic differences between DNA restriction fragments caused by nucleotide sequence variability. Thus, the present invention further provides a means to follow segregation of a gene or nucleic acid of the present invention as well as chromosomal sequences genetically linked to these genes or nucleic acids using such techniques as RFLP analysis.

Plants that can be used in the method of the invention include monocotyledonous and dicotyledonous plants. Preferred plants include corn, soybean, sunflower, sorghum, canola, wheat, alfalfa, cotton, rice, barley and millet.

Seeds derived from plants regenerated from transformed plant cells, plant parts or plant tissues, or progeny derived from the regenerated transformed plants, may be used directly as feed or food, or further processing may occur.

Expression of the inventive nucleic acids in plants, such as corn is expected to enhance growth and biomass accumulation. Other more specialized applications exist for these nucleic acids at the whole plant level. It has been demonstrated that endoreduplication occurs in numerous cell types within plants, but this is particularly prevalent in maize endosperm, the primary seed storage tissue. Under the direction of endosperm-specific promoters, expression of cell cycle genes (and possibly expression of such genes in conjunction with genes that inhibit mitosis) will further stimulate the process of endoreduplication.

The nucleic acids and polypeptides of the present invention can be used to identify interacting proteins involved in cell cycle regulation. Fragments of the present polypeptides can be used as antigens. The nucleic acids of the present invention can be used to modulate the expression of the WEE1 polypeptide in plants. Modulating the nucleic acids and polypeptides of the present invention is expected to increase or decrease the number of cells undergoing cell division in a plant. Modulating Wee1 nucleic acids is expected to increase crop yield. Based on experiments with CycD nucleic acids, it is expected that introduction of antisense Wee1 nucleic acids and polypeptides will improve transformation frequencies and efficiency in cells from various sources. Antisense WEE1 nucleic acids are expected to provide a positive growth advantage in a plant. Abrogation of WEE1 activity by antisense nucleic acids or other methods mentioned supra are expected to decrease the effect of stresses on cell cycle progression.

The present invention will be further described by reference to the following detailed examples. It is understood, however, that there are many extensions, variations, and modifications on the basic theme of the present invention beyond that shown in the examples and description, which are within the spirit and scope of the present invention. All publications, patents, and patent applications cited herein are hereby incorporated by reference.

EXAMPLES

Example 1

Plant Materials. Maize (*Zea mays* L.) inbred line W64A$^+$ was grown at the University of Arizona research farm in Tucson during 1995 and 1996. Immature ears and developing kernels were harvested, frozen in liquid nitrogen and stored at −80° C. For RNA extraction, the embryo and scutellum were removed by hand dissection. Protein extractions were performed in NETN (20 mM Tris-HCl, pH 8.5, 100 mM NaCl, 1 mM EDTA, 1 mM DTT, and 0.5% Triton-X100) supplemented with 5 mM NaF, 1 mM sodium orthovanadate and 0.1 mM PMSF.

Isolation of a zmwee1 cDNA clone from maize endosperm. A cDNA homologous to wee1 was identified in the maize EST database at Pioneer Hi-Bred Int. (Johnston, Iowa). The corresponding DNA was labeled with $^{32}$P and used to screen a λZapII cDNA library constructed from 9 DAP endosperm (Sun et al., 1997). Plaque lifting and hybridization were performed as described as previously (Habben et al., 1993).

Expression of zmwee1 in *E. coli*. Through the use of primer A (5'-ATCGGATCC-GCACGAGTCTGCACCCCG-3') and primer B (5'-TCGAATTCGTGATGGTGATGGTG-ATGCTTCGATGAGGCCTTGTG-3'), the coding region of zmwee1 was amplified using Taq polymerase (Gibco) by PCR with 35 cycles at 95° C. for 1 min, 65 C for 2 min and 72° C. for 3 min. After digestion with Nde1 and Bam H1, the 1.2 kb zmwee1 fragment was cloned into the Bam H1 and Eco R1 sites of pGEX 2T (Pharmacia Biotech Products, Piscataway, N.J.) to create a GST fusion construct, pGEX2Tzmwee1. Recombinant GST-ZMWEE1 protein was isolated as described by Frangioni et al. (Frangioni et al., 1993). *E. coli* lysate was applied to a glutathione agarose column and washed with NETN. Maize WEE1 protein, GST-ZMWEE1, was eluted with 10 mM reduced glutathione (50 mM Tris-HCl, pH 8.0; 1 mM DTT and 0.1% Triton-X100). The protein concentration was determined by the Bradford assay (BioRad, Hercules, Calif.) with albumin standard from Pierce (Rockford, Ill.).

ZMWEE1 produced in *E. coli* inhibits MPF activity. To analyze the CDK inhibitory activity of maize WEE1, we cloned zmwee1 into an expression vector, pGEX 2T, to create pGEXzmwee1. The resulting glutathione S-transferase (GST) ZMWEE1 fusion protein was purified by affinity chromatography on glutathione agarose. The purified recombinant protein was then tested for CDK inhibitory activity. We prepared maize CDK by incubating p13$^{suc1}$ agarose with extracts of immature ear, which exhibits high mitotic activity. Neither GST nor the crude immature ear extract inhibited the CDK adsorbed by p13$^{suc1}$, but GST-ZMWEE1, with or without pre-incubation, inhibited CDK activity. To analyze the proportion of CDK that is susceptible to the inhibition of GST-ZMWEE1, we incubated GST-ZMWEE1 with crude extracts from immature ear. GST-ZMWEE1 inhibits the histone H1-kinase activity in the extract. This result shows that all the detectable EGTA-insensitive histone H1 kinase activity in the immature ear is susceptible to inhibition by GST-ZMWEE1.

Cyclin-dependent protein kinase (CDK) inhibition was determined by adding purified GST-ZMWEE1 to maize MPF prepared from immature ear with p13$^{suc1}$ agarose (Grafi and Larkins 1995). The enzyme was pre-incubated 15 min in EB buffer (80 mM β-glycerophosphate, pH 7.5; 20 mM EGTA; 15 mM MgCl2; 1 mM DTT; 0.05 mM PMSF and 5 μg/ml aprotinin) in the presence of 0.1 mM ATP. Histone H1 kinase activity was analyzed as described previously (Grafi and Larkins, 1995).

Over-expression of zmwee1 in *Schizosaccharomyces pombe*.

zmwee1 was cloned into pREP1, an *S. pombe* expression vector containing the thiamine-suppressable promoter, NMT1$^+$(Maundrell, 1993). *S. pombe* cells transformed with pREP1 grow normally (FIG. 1), while over expression of ZMWEE1 significantly inhibited cell division and caused the cells to increase in size.

The coding sequence of zmwee1 was amplified by PCR under the conditions described above using primers 5'-GTCCATATGGCACGAGTCTGCACCC-CGGAC-3' and

5'-TAGGGATCCCTTCGATGAGGCCTTGTG-3'.

The 1.2 kb fragment was ligated into the Nde I and Bam HI sites of pREP1 (Maundrell, 1993) to create pREP1zmwee1. Transformation of *S. pombe* (PR109, -leu1, -ura4) was based on a protocol for transforming *S. cerevisiae* (Bai and Elledge, 1996) with modifications. Ten ml of the yeast suspension culture was centrifuged at 5K in a bench top centrifuge. The pellet was washed once with 5 ml of sterilized water, once with 2.5 ml of LiSorb (10 mM Tris-HCl, pH 8; 100 mM LiOAc; 1 mM EDTA and 1 M Sorbitol) and resuspended the in 0.6 ml of LiSorb. Fifty μl of the suspension was mixed with 50 μl of plasmid DNA solution (LiSorb containing 10 μg of pREPzmwee1 and 200 μg of sheared Salmon Sperm DNA) prior to adding 900 μl of LiAc/TE (10 mM Tris-HCl, pH 8; 100 mM LiOAc and 1 mM EDTA). The mixture was incubated at 30° C. for 30 min and heat shocked at 42° C. for 7 min. An aliquot of 250 μl was plated onto an EMM plate (Moreno et al., 1991) and incubated at 26° C. for four days. The morphology of the transformants was analyzed with a ZEISS light microscope.

RNA gel blotting RNA was isolated from 4 day old seedlings and endosperm at 9, 11, 13, 15 and 17 days after pollination (DAP) as described by Jones et al.(1985) with the following modifications. Ten grams of tissue was frozen in liquid nitrogen, ground into powder with a mortar and pestle and resuspended in 10 ml of 50 mM Tris-HCl, pH 7.5, 10 mM EDTA, 1% SDS, 1.5M NaCl. The sample was extracted once with one volume of phenol:chloroform:isoamyl-alcohol (24:24:1) and once with one volume of chloroform:isoamyl-alcohol (24:1). RNA was precipitated with two volumes of ethanol and resuspended in diethylpyrocarbonate (DEPC)-treated water; LiCl was added to a final concentration of 2.8 M. The RNA was incubated on ice 30 min and concentrated by centrifugation at 10,000×g. The pellet was washed with 3M LiCl and resuspended in DEPC-treated water. Poly(A)$^+$ RNA was isolated by oligo (dT) cellulose chromatography according to manufacture's instructions (Promega, Madison, Wis.). Five μg of poly(A) RNA from maize endosperm or 30 μg of total RNA from young seedlings was loaded on agarose gels, electrophoresed in the presence of 20% formaldehyde, transferred to a nylon membrane and probed with $^{32}$P-labeled zmwee1.

Molecular cloning of zmwee1. An 807 bp EST was identified in the Pioneer EST database that shows 36% identity to the amino acid sequence of Drosophila WEE1. Using this clone as a probe, we screened a maize endosperm cDNA library constructed with poly(A) RNA from 9 DAP endosperm (Sun et al., 1997). The analysis of 400,000 plaques led to the identification of two identical clones designated zmwee1. The nucleotide sequence of zmwee1 is identical to Pioneer's EST sequence with an 807 bp overlap. ZMWEE1 is 1601 bp in length with a large open reading frame of 1211 bp. It encodes a protein of 403 amino acid residues with a calculated molecular size of 45.6 kD. Since a translation initiation sequence was not detected in the deduced nucleotide sequence and the ZMWEE1 transcript is approximately 2.4 kb (see below), we believe zmwee1 encodes only a portion of the maize wee1 sequence.

zmwee1 is a single locus on maize chromosome 4. A database search with zmwee1 identified a maize RFLP marker, UMC169, as zmwee1. This genomic DNA fragment, generated as part of a genome mapping project at the University of Missouri, contains three exon regions found in zmwee1. Mapping experiments placed this locus at the bottom of the long arm of chromosome 4 at position 187.4, bin 4.11.

zmwee1 transcripts accumulate in endosperm during the period of endoreduplication. To investigate the expression of zmwee1 in maize, we performed RNA gel blot analyses with transcripts from different tissues, including endosperm at several developmental stages. zmwee1 RNA accumulated in the endosperm between 9 and 17 DAP, reaching a maximum level at 15 DAP. This coincides with the period when endosperm nuclei are undergoing the maximum rate of endoreduplication (Grafi and Larkins, 1995; Y. Sun and B. Dilkes, unpublished data). In young seedlings, the zmwee1 transcript was easily detectable in 30 μg of total RNA and corresponded to a transcript of approximately 2.4 kb. The abundance of zmwee1 RNA is highest in young seedlings, as compared to leaf, root and endosperm tissues.

Example 2

Using wee1 in a Two-Hybrid System to Identify Maize Cell Cycle Genes

Wee1 gene expression during the G2→M transition and during mitosis plays a prominent role in controlling progression through the cell cycle. The encoded protein is an important part of the checkpoint control machinery that regulates p34$^{cdc2}$ activity and it's participation in the active MPF (maturation promoting factor) complex. In turn, WEE1 activity can be stimulated by the CDK2-cyclinA complex, or inhibited by nim1. As such, the wee1 gene and its encoded protein can be used to identify other cell cycle regulatory proteins. This can be done using the wee1 gene as bait (the target fused to the DNA-binding domain) in a yeast two-hybrid screen. Methods for two-hybrid library construction, cloning of the reporter gene, cloning of the DNA-binding and activation domain hybrid gene cassettes, yeast culture, and transformation of the yeast are all done according to well-established methods (see Sambrook et al., 1990; Ausubel et al., 1990; Hannon and Bartels, 1995). Using this method, nim1, CDK1, and possibly CDK2 are identified as components of the activation domain hybrid, and are confirmed through further sequence analysis.

Example 3

Overexpression of wee1 Causes Cell Cycle Arrest

To demonstrate this, a chemically-inducible promoter is used. The wee1 gene is cloned into a cassette with an inducible promoter such as the estrogen-inducible promoter (for example, in a cassette containing 4×ERE::zmwee1::pinII). Either particle-mediated DNA delivery or Agrobacterium-mediated delivery are used to introduce the 4×ERE::zmwee1::pinII-containing plasmid along with a-UBI::bar::pinII-containing plasmid into maize cells capable of growth on suitable maize culture medium. Such competent cells can be from maize suspension culture, callus culture on solid medium, freshly isolated immature embryos or meristem cells. Immature embryos of the Hi-II genotype are used as the target for co-delivery of these two plasmids, and within 1–7 days the embryos are moved onto culture medium containing 3 mg/1 of the selective agent bialaphos. Embryos, and later callus, are transferred to fresh selection plates every 2 weeks. After 6–8 weeks, transformed calli are recovered.

Transgenic callus containing both genes can be verified using PCR and Southern analysis. Northern analysis can also be used to verify which calli are expressing the bar gene but not expressing wee1 at levels above normal wild-type cells (based on hybridization of probes to freshly isolated mRNA population from the cells). Upon exposure to estrogen (or estradiol), wee1 is expressed (this can be confirmed by Northern analysis). This induced wee1 overexpression results in phosphorylation of p34 at tyrosine-15 (inactivating p34), effectively blocking the transition from G2 into mitosis.

Cytological methods can be used to verify decreased frequencies of progression from G2-phase into mitosis (i.e. for cells in which a visual marker such as GFP was transformed alongside wee1 the green fluorescent cells will exhibit a lower mitotic index). Cells in S-phase (undergoing DNA replication) can be monitored by detecting nucleotide analog incorporation.

For example, following incubation of cells with bromodeoxyuridine (BrdU) incorporation of this thymidine analog can be detected by methods such as antiBrdU immunocytochemistry or through enhancement of Topro3 fluorescence. By blocking the cell cycle before mitosis, wee1 expression will decrease the proportion of cells incorporating BrdU (i.e. a lower percentage of transformed cells will incorporate BrdU relative to untransformed cells).

Blockage of the cell cycle before mitosis can also be monitored using such methods as flow cytometric analyses (FCS) of protoplasts (or nuclei), in conjunction with appropriate BrdU-insensitive fluorescent DNA labels such as propidium iodide and DAPI or BrdU-detecting methods described above. For example, tissue is homogenized to release nuclei that are analyzed using the FCS for both green fluorescence (from our accompanying GFP marker) and DNA content. Such FCS analysis demonstrates that expression of a co-transformed GFP reporter correlates with wee1-induced changes in the ratios of cells in G1, S and G2 (increased proportion in G2, for example). Similar experiments can be run using the fluorescently labeled anti-BrdU antisera to demonstrate that wee1 expression decreases the percentage of cells in S-phase.

Cell cycle stage-specific probes can also be used to monitor cell cycle progression. For example, numerous spindle-associated proteins are expressed during a fairly narrow window during mitosis, and antibodies or nucleic acid probes to cyclins, histones, or DNA synthesis enzymes can be used as positive markers for the G1/S transition. For cells that have received the wee1 gene cassette, blockage of the cell cycle is manifested in a decreased mitotic index, detected by staining for mitotic figures using a DNA dye such as DAPI or Hoechst 33258.

FCS analysis of wee1-expressing cells shows that a high percentage of cells are in G2 phase (consistent with failure to progress from G2 to mitosis). Cells arrested in G2 (before the transition into mitosis) will have an elevated DNA content. FCS analysis of wee1-expressing cells shows that a high percentage of cells contain an elevated DNA content (4N or greater if cells are undergoing endoreduplication). The percentage of cells labeled with cell cycle stage-specific probes is altered, as mentioned above.

Example 4

Expression of wee1 Using Tissue-Specific or Cell-Specific Promoters Blocks the Transition from G2 into Mitosis wee1 gene expression using tissue-specific or cell-specific promoters blocks cell cycle progression in the expressing tissues or cells, effectively preventing entry into mitosis. For example, using a microspore- or tapetum-specific promoter effectively blocks pollen and/or anther development, rendering such expressing plants male sterile. Alternatively, driving wee1 expression with a strongly expressed, early, tassel-specific promoter will inhibit development of this entire reproductive structure.

Expression of wee1 genes in other cell types and/or at different stages of development will only block G2/M (for example in endosperm cells or in certain leaf cells).

It is envisaged that retarding or eliminating development of other plant parts could also be affected through similar tissue-specific expression during growth.

Example 5

Expression of the wee1 Gene can be Used to Manipulate Endoreduplication wee1 expression effectively prevents progression from G2 into mitosis. Further, it has been shown that wee1 is expressed in tissues such as the endosperm where endoreduplication is occurring (during this process, S-phase occurs repeatedly, without intervening mitoses). Thus, stimulating expression of wee1 above levels normally observed in a given cell type while concomitantly overexpressing a gene that stimulates the G1/S transition would promote endoreduplication. Endoreduplication in various cell types, including for example endosperm and leaf, has been correlated with changes such as increased cell size, increased protein synthesis and accumulation, etc. Thus, manipulation of wee1 expression in conjunction with S-phase stimulating genes would be expected to also result in similar cellular changes (i.e. increased cell size, protein content etc.). This could be accomplished by expressing wee1 in conjunction with another transgene (or genes) that stimulate the G1/S phase transition (for example, cyclin-D, cyclin-E, E2F and others). Alternately this could be accomplished, by expressing wee1 in cells where an accelerated G1/S phase transition is taking place or elevated levels of G1/S phase activators are already accumulating.

Example 6

Transient wee1-Antisense Expression Stimulates Cell Division and Enhances Transgene Integration The delivery of damaged DNA, (similar to what we introduce by particle gun delivery methods) induces checkpoint controls and inhibits cell cycle progression. This inhibition can be obviated by transient down-regulation of negative regulators such as wee1. Regardless of the mechanism of arrest; i.e. presence of damaged DNA or delivery into a non-cycling differentiated cell, stimulation of the cell cycle will increase integration frequencies.

To demonstrate this, a wee1-antisense sequence is cloned into a cassette with a constitutive promoter (i.e. either a strong maize promoter such as the ubiquitin promoter including the first ubiquitin intron, or a weak constitutive promoter such as nos). Delivery of the wee1-antisense DNA in an appropriate plant expression cassette (for example, in a UBI::zmwee1-antisense::pinII-containing plasmid) along with UBI::bar::pinII can be accomplished through numerous well-established transformation methods for plant cells.

Using a suitable method, DNA is introduced into maize cells capable of growth on suitable maize culture medium. Such competent cells can be from maize suspension culture, callus culture on solid medium, freshly isolated immature embryos or meristem cells. Immature embryos of the Hi-II genotype are used as the target for co-delivery of these two plasmids. Transient expression of the wee1-antisense down-regulates WEE1, which in turn releases the cells to progress through the cell cycle and divide.

Cytological methods can be used to verify increased frequencies of progression through mitosis (i.e. for cells in which a visual marker such as GFP was transformed alongside wee1-antisense the green fluorescent cells will exhibit a higher mitotic index; as discussed in earlier examples).

To assess the effect on transgene integration, growth of bialaphos-resistant colonies on selective medium is a reliable assay. Within 1–7 days after DNA introduction, the embryos are moved onto culture medium containing 3 mg/l of the selective agent bialaphos. Embryos, and later callus, are transferred to fresh selection plates every 2 weeks. After 6–8 weeks, transformed calli are recovered. Transgenic callus containing the introduced genes can be verified using PCR and Southern analysis. Northern analysis can also be used to verify which calli are expressing the bar gene, and/or the wee1-antisense construct. In immature embryos that had transient, elevated wee1-antisense expression, higher numbers of stable transformants are recovered (likely a direct result of increased integration frequencies). Increased transgene integration frequency can also be assessed using such well-established labeling methods such as in situ hybridization.

For this specific application (using transient wee1-antisense-mediated cell cycle stimulation to increase transient integration frequencies), it may be desirable to reduce the likelihood of ectopic stable expression of wee1-antisense. Strategies for transient-only expression can be used. This includes delivery of RNA (transcribed from the wee1-antisense construct) along with the transgene cassettes to be integrated to enhance transgene integration by transient stimulation of cell division. Using well-established methods to produce wee1-antisense-RNA, this can then be purified and introduced into maize cells using physical methods such as microinjection, bombardment, electroporation or silica fiber methods.

Example 7

Use of Antisense Oligonucleotides against wee1 to Transiently Stimulate Cell Division and Enhance Transgene Integration An alternative to conventional antisense strategies is the use of antisense oligonucleotides (often with chemically modified nucleotides). Such an antisense oligonucleotide, typically a 15–18mer (but this size can vary either more or less), is designed to bind around accessible regions such as the ribosomal binding site around the "Start" codon. Introduction of the antisense oligonucleotide into a cell will transiently stop expression of the targeted gene. For example, an antisense oligonucleotide of between 15 to 18 nucleotides in length, that is complementary (in reverse orientation) to the sequence surrounding the Start codon of the wee1 structural gene, is introduced into maize cells. These methods of introduction for the oligonucleotide are similar to those previously described above for introduction of plasmids. In cells that receive such an antisense oligonucleotide targeted to wee1, the antisense oligonucleotide transiently disrupts wee1 expression and stimulates entry into mitosis (as observed in mammalian cells—see Nuell et al., 1991, Mol. and Cell. Biology 11(3):1372–1381).

Example 8

Use of Antibodies Raised against WEE1 to Transiently Stimulate Cell Division and Enhances Transgene Integration Antibodies directed against WEE1 can also be used to mitigate WEE1's activity, thus stimulating the cell cycle and transgene integration. Genes encoding single chain antibodies, expressed behind a suitable promoter, for example the ubiquitin promoter could be used in such a fashion. Transient expression of an anti-WEE1 antibody could temporarily disrupt normal WEE1 function and thus stimulate the cell cycle. Alternatively, antibodies raised against WEE1 could be purified and used for direct introduction into maize cells. The antibody is introduced into maize cells using physical methods such as microinjection, bombardment, electroporation or silica fiber methods. Alternatively, single chain anti-WEE1 is delivered from *Agrobacterium tumefaciens* into plant cells in the form of fusion's to Agrobacterium virulence proteins.

Fusion's are constructed between the anti-WEE1 single chain antibody and bacterial virulence proteins such as VirE2, VirD2, or VirF which are known to be delivered directly into plant cells. Fusion's are constructed to retain both those properties of bacterial virulence proteins required to mediate delivery into plant cells and the anti-WEE1 activity required for stimulating cell division and enhancing transgene integration. This method ensures a high frequency of simultaneous co-delivery of T-DNA and functional anti-WEE1 protein into the same host cell. Direct delivery of anti-WEE1 antibodies using physical methods such as particle bombardment can also be used to inhibit WEE1 activity and transiently stimulate G2/M transition.

The methods above represent various means of using the wee1-antisense or anti-WEE1 antibodies or antisense oligonucleotides to transiently stimulate cell division, which in turn enhances transgene integration by providing an improved cellular/molecular environment for this event to occur.

Example 9

Altering WEE1 Activity Stimulates the Cell Cycle and Growth

Based on results in other eukaryotes, expression of the zmwee1 gene should block the G2/M transition and prevent cell division. This decrease in division rate is assessed in a number of different manners, being reflected in larger cell size, less rapid incorporation of radiolabeled nucleotides, and slower growth (i.e. less biomass accumulation). Conversely, expression of wee1 antisense (or an appropriate antisense oligonucleotide, or anti-WEE1 antibody) will result in smaller cells, more rapid incorporation of radiolabeled nucleotides, and faster growth. Delivery of the wee1-antisense in an appropriate plant expression cassette is accomplished through numerous well-established methods for plant cells. As an alternative to conventional delivery of bacterial plasmids, introduction of a viral plasmid from which a wee1-antisense sequence is expressed could also be employed.

The result of zmwee1-antisense expression will be to stimulate cell division, providing the optimal cellular environment for integration of introduced genes. This will trigger a tissue culture response (cell divisions) in genotypes that typically do not respond to conventional culture techniques, or stimulate growth of transgenic tissue beyond the normal rates observed in wild-type (non-transgenic) tissues.

To demonstrate this, the wee1-antisense gene is cloned into a cassette with a constitutive promoter (i.e. either a strong maize promoter such as the ubiquitin promoter including the first ubiquitin intron or a weak constitutive promoter such as nos). Either particle-mediated DNA delivery or Agrobacterium-mediated delivery are used to introduce the UBI::zm-wee1-antisense::pinII-containing plasmid along with a UBI::bar:pinII-containing plasmid into maize cells capable of growth on suitable maize culture medium. Such competent cells can be from maize suspension culture, callus culture on solid medium, freshly isolated immature embryos or meristem cells. Immature embryos of the Hi-II genotype are used as the target for co-delivery of these two plasmids, and within 1–7 days the embryos are moved onto culture medium containing 3 mg/l of the selective agent bialaphos. Embryos, and later callus, are transferred to fresh selection plates every 2 weeks. After 6–8 weeks, transformed calli are recovered. In treatments where both the bar gene and wee1-antisense gene have been transformed into immature embryos, a higher number of growing calli are recovered on the selective medium and callus growth is stimulated (relative to treatments with the bar gene alone).

When the wee1-antisense gene is introduced without any additional selective marker, transgenic calli can be identified by their ability to grow more rapidly than surrounding wild-type (non-transformed) tissues. Transgenic callus can be verified using PCR and Southern analysis. Northern analysis can also be used to verify which calli are expressing the bar gene, and which are expressing the maize wee1 gene at levels above normal wild-type cells (based on hybridization of probes to freshly isolated mRNA population from the cells).

Inducible Expression

The wee1-antisense gene can also be cloned into a cassette with an inducible promoter such as the benzenesulfonamide-inducible promoter. The expression vector is co-introduced into plant cells and after selection on bialaphos, the transformed cells are exposed to the safener (inducer). This chemical induction of wee1-antisense expression results in stimulated G2/M transition and more rapid cell division. The cells are screened for the presence of zmwee1-antisense RNA by northern, or RT-PCR (using transgene specific probes/oligo pairs). Various cell cycle division assays could be employed, as described above.

Example 10

Control of wee1-Antisense, (or Anti-WEE1 Antibody) Expression Using Tissue-Specific or Cell-Specific Promoters Provides a Differential Growth Advantage wee1-antisense (or anti-WEE1 antibody) expression using tissue-specific or cell-specific promoters stimulates cell cycle progression in the expressing tissues or cells. For example, using a seed-specific promoter will stimulate cell division rate and result in increased seed biomass. Alternatively, driving wee1-antisense (or anti-WEE1 antibody) expression with a strongly expressed, early, tassel-specific promoter will enhance development of this entire reproductive structure. Expression in other cell types and/or at different stages of development will similarly stimulate cell division rates.

Example 11

Meristem Transformation

Meristem transformation protocols rely on the transformation of apical initials or cells that can become apical initials following reorganization due to injury or selective pressure. The progenitors of these apical initials differentiate to form the tissues and organs of the mature plant (i.e. leaves, stems, ears, tassels, etc.). The meristems of most angiosperms are layered with each layer having its own set of initials. Normally in the shoot apex these layers rarely mix. In maize the outer layer of the apical meristem, the L1, differentiates to form the epidermis while descendents of cells in the inner layer, the L2, give rise to internal plant parts including the gametes. The initials in each of these layers are defined solely by position and can be replaced by adjacent cells if they are killed or compromised. Meristem transformation frequently targets a subset of the population of apical initials and the resulting plants are chimeric. If for example, 1 of 4 initials in the L1 layer of the meristem are transformed only ¼ of epidermis would be transformed. Selective pressure can be used to enlarge sectors but this selection must be non-lethal since large groups of cells are required for meristem function and survival.

Transformation of an apical initial with a wee1-antisense (or anti-WEE1 antibody) sequence under the expression of a promoter active in the apical meristem (either meristem-specific or constitutive) would allow the transformed cells to grow faster and displace wild-type initials driving the meristem towards homogeneity and minimizing the chimeric nature of the plant body. To demonstrate this, the wee1-antisense (or anti-WEE1 antibody) sequence is cloned into a cassette with a promoter that is active within the meristem (i.e. either a strong constitutive maize promoter such as the ubiquitin promoter including the first ubiquitin intron, or a promoter active in meristematic cells such as the maize histone, cdc2 or actin promoter). Coleoptilar stage embryos are isolated and plated meristem up on a high sucrose maturation medium (see Lowe et al., 1997, In *Genetic Biotechnology and Breeding of Maize and Sorghum*, AS Tsaftaris, ed., Royal Society of Chemistry, Cambridge, UK, pp. 94–97).

The wee1-antisense (or anti-WEE1) expression cassette along with a reporter construct such as Ubi:GUS:pinII can then be co-delivered (preferably 24 hours after isolation) into the exposed apical dome using conventional particle gun transformation protocols. As a control the wee1-antisense (or anti-WEE1) construct can be replaced with an equivalent amount of pUC plasmid DNA. After a week to 10 days of culture on maturation medium the embryos can be transferred to a low sucrose hormone-free germination medium. Leaves from developing plants can be sacrificed for GUS staining. Transient expression of the wee1-antisense (or anti-WEE1) sequence in meristem cells, through stimulation of the G2/M transition, will result in greater integration frequencies and hence more numerous transgenic sectors. Integration and expression of the wee1- antisense (or anti-WEE1) sequence will impart a competitive advantage to expressing cells resulting in a progressive enlargement of the transgenic sector. Due to the enhanced growth rate in wee1-antisense (or anti-WEE1) expressing meristem cells, they will supplant wild-type meristem cells as the plant continues to grow. The result will be both enlargement of transgenic sectors within a given cell layer (i.e. periclinal expansion) and into adjacent cell layers (i.e. anticlinal invasions). As cells expressing the wee1-antisense (or anti-WEE1 antibody) occupy an increasingly large proportion of the meristem, the frequency of transgene germline inheritance goes up accordingly.

Example 12
Use of Flp/Frt System to Excise the wee1-Antisense (or Anti-WEE1 Antibody) Expression Cassette In cases where the wee1-antisense (or anti-WEE1 antibody) has been integrated and expression is useful in the recovery of maize transgenics, but is ultimately not desired in the final product, the wee1-antisense (or anti-WEE1 antibody) expression cassette (or any portion thereof that is flanked by appropriate FRT recombination sequences) can be excised using FLP-mediated recombination (see pending U.S. patent application Ser. No. 08/972,258 filed Nov. 18, 1997).

What is claimed is:

1. An isolated wee1 nucleic acid comprising a member selected from the group consisting of:
   (a) a polynucleotide that encodes a polypeptide of SEQ ID NO: 2;
   (b) a wee1 polynucleotide having at least 80% identity to the entire coding region of SEQ ID NO: 1;
   (c) a polynucleotide comprising the coding sequence set forth in SEQ ID NOS: 1; and
   (d) a polynucleotide complementary to a polynucleotide of (a) through (c).

2. An isolated nucleic acid encoding a polypeptide capable of modulating wee1 activity, the isolated nucleic acid comprising a polynucleotide that encodes a polypeptide of SEQ ID NO: 2 or a polynucleotide complementary thereof.

3. An isolated nucleic acid encoding a polypeptide capable of modulating wee1 activity, the isolated nucleic acid comprising a polynucleotide having at least 80% identity to the entire coding region of SEQ ID NO: 1, wherein the percent identity is determined by the Gap 10 program in the Wisconsin Genetics Software Package using default parameters, or a polynucleotide fully complementary thereof.

4. The isolated nucleic acid of claim 3, wherein the polynucleotide has at least 90% identity.

5. The isolated nucleic acid of claim 4, wherein the polynucleotide has at least 95% identity.

6. An isolated nucleic acid encoding a polypeptide capable of modulating wee1 activity, the isolated nucleic acid comprising a polynucleotide comprising the coding sequence set forth in SEQ ID NOS: 1 or a polynucleotide fully complementary thereof.

7. The isolated nucleic acid of claim 1 wherein the wee1 polynucleotide is a maize wee1 polynucleotide.

8. The isolated nucleic acid of claim 1 adducted to a second nucleic acid sequence encoding a DNA-binding domain.

9. A vector comprising at least one nucleic acid of claim 1.

10. An expression cassette comprising at least one nucleic acid of claim 1 operably linked to a promoter, wherein the nucleic acid is in sense or antisense orientation.

11. A bacterial, yeast, insect or plant cell into which is introduced at least one expression cassette of claim 10.

12. The plant cell of claim 11 that is a monocot or dicot plant cell.

13. A transgenic plant comprising at least one expression cassette of claim 10.

14. The transgenic plant of claim 13, wherein the plant is corn, soybean, sunflower, sorghum, canola, wheat, alfalfa, cotton, rice, barley and millet.

15. A transgenic seed comprising the expression cassette of claim 10.

16. The seed of claim 15, wherein the seed is from corn, soybean, sunflower, sorghum, canola, wheat, alfalfa, cotton, rice, barley and millet.

17. An isolated ribonucleic acid sequence encoding a protein having the sequence of SEQ ID NO: 2.

* * * * *

UNITED STATES PATENT AND TRADEMARK OFFICE
CERTIFICATE OF CORRECTION

PATENT NO.    : 6,777,590 B2
DATED         : August 17, 2004
INVENTOR(S)   : Sun et al.

Figure 2:
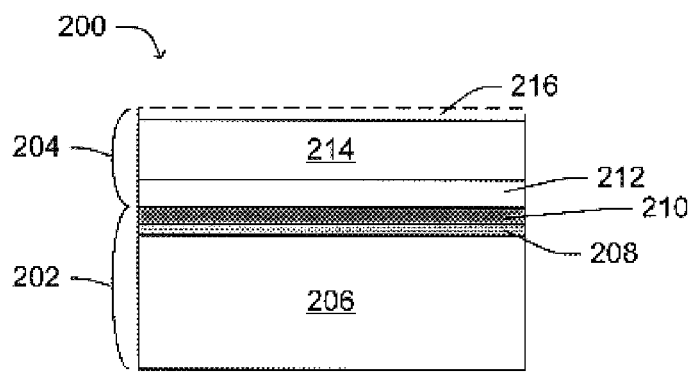
Figure 1:
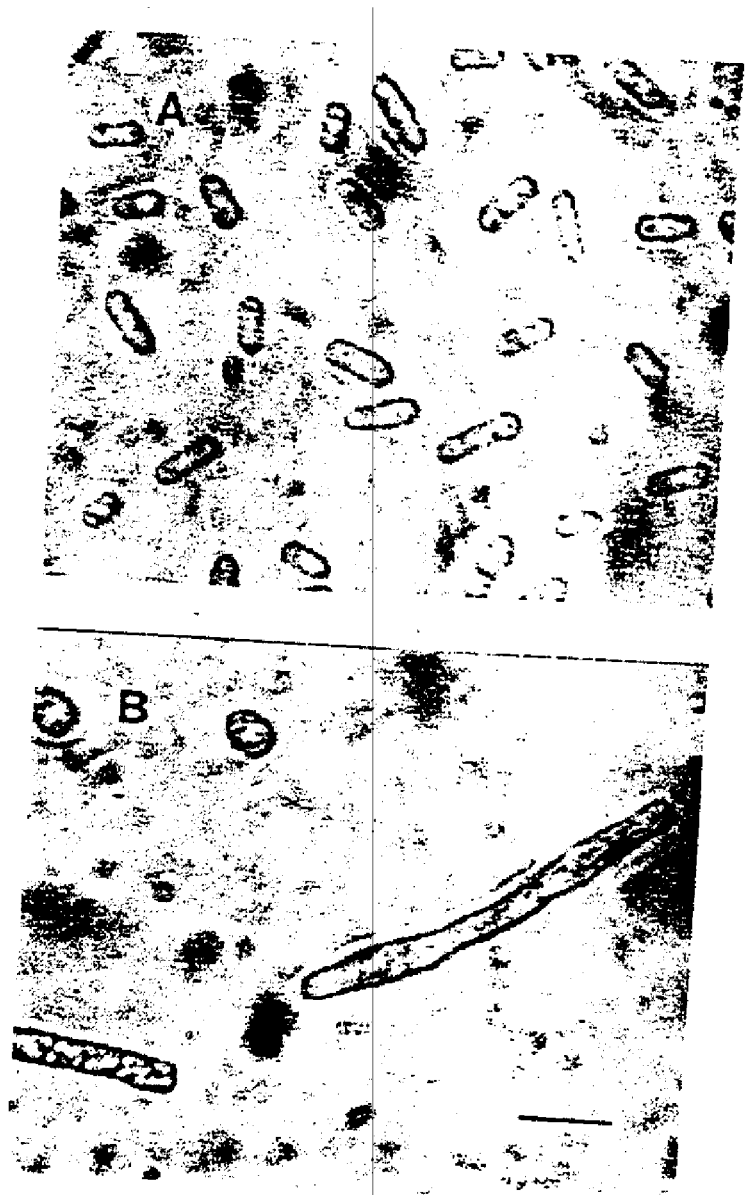

It is certified that error appears in the above-identified patent and that said Letters Patent is hereby corrected as shown below:

Drawings,
Delete Fig. 1 and Fig. 2 and insert attached Fig. 1.

Signed and Sealed this

Tenth Day of May, 2005

JON W. DUDAS
*Director of the United States Patent and Trademark Office*

UNITED STATES PATENT AND TRADEMARK OFFICE
CERTIFICATE OF CORRECTION

PATENT NO. : 6,777,590 B2
DATED : August 17, 2004
INVENTOR(S) : Sun et al.

It is certified that error appears in the above-identified patent and that said Letters Patent is hereby corrected as shown below:

Column 1,
Line 7, before "TECHNICAL FIELD", insert the following paragraph:

-- STATEMENT REGARDING FEDERALLY SPONSORED RESEARCH OR DEVELOPMENT

This invention was made with Government support under Contract No. DE-FG03-95ER20183 awarded by the Department of Energy. The Government has certain rights in this invention. --.

Signed and Sealed this

Sixth Day of September, 2005

JON W. DUDAS
*Director of the United States Patent and Trademark Office*